United States Patent [19]

Adelman et al.

[11] Patent Number: 5,744,594

[45] Date of Patent: Apr. 28, 1998

[54] DNA ENCODING ATP-SENSITIVE POTASSIUM CHANNEL GENES

[75] Inventors: John P. Adelman; Michael J. Ashford; Chris T. Bond, all of Portland, Oreg.

[73] Assignee: Oregon Health Sciences University, Portland, Oreg.

[21] Appl. No.: 385,186

[22] Filed: Feb. 7, 1995

Related U.S. Application Data

[63] Continuation-in-part of Ser. No. 288,510, Aug. 10, 1994, which is a continuation-in-part of Ser. No. 193,372, Feb. 8, 1994, abandoned.

[51] Int. Cl.⁶ .......................... C07H 21/02; C07H 21/04
[52] U.S. Cl. ............................ 536/23.2; 536/23.5
[58] Field of Search ....................... 536/23.2, 23.5, 536/23.1

[56] References Cited

U.S. PATENT DOCUMENTS 5,356,775  10/1994  Hebert et al. ........................ 435/6

OTHER PUBLICATIONS

Cook, Daniel L., et al. (1984) "Intracellular ATP directly blocks $K^+$ channels in pancreatic B–cells", *Nature* 311:271–273.

Ashcroft, Frances M., et al. (1984) "Glucose induces closure of single potassium channels in isolated rat pancreatic β–cells", *Nature* 312:446–448.

Misler, Stanley, et al. (1986) "A metabolite–regulated potassium channel in rat pancreatic B cells", *Proc. Natl. Acad. Sci.* 83:7119–7123.

Ashcroft, Frances M. (1988) "Adenosine 5'–Triphosphate–Sensitive Potassium Channels", *Ann. Rev. Neurosci.* 11:97–118.

Standen, Nicholas Bo, et al. (1989) "Hyperpolarizing Vasodialators Activate ATP–Sensitive $K^+$ in Artenal Smooth Muscle", *Science* 245:177–180.

Quast, Ulrich, et al. (1989) "Moving together: K+ channel openers and ATP–sensitive K+ channels", *TiPS* 10:431–435.

Ashford, Michael L.J., et al. (1990) "Glucose–induced excitation of hypothalamic neurones is mediated by ATP–sensitive K+ channels", *European Journal of Physiology* 415:479–483.

Fan, Zheng, et al. (1990) "Pinacidil activates the ATP–sensitive K+ channel in inside–out and cell–attached patch membranes of guinea–pig ventricular myocytes", *European Journal of Physiology* 415:387–394.

Daut, Jürgen, et al. (1990) "Hypoxic Dilation of Coronary Arteries is Mediated by ATP–Sensitive Potassium Channels", *Science* 247:1341–1344.

Kirsch, G.E., et al. (1990) "Coupling of ATP–sensitive K+ channels to $A_1$ receptors by G proteins in rat ventricular myocytes", *American Physiology Society* H820–H826.

Nichols, C.G. et al. (1991) "Adenosine triphosphate–sensitive potassium channels in the cardiovascular system", *Invited Review* H1675–H1686.

Janigro, Damir, et al. (1993) "ATP–sensitive K+ channels in rat aorta and brain microvascular endothelial cells", *American Physiological Society* C812–C821.

Edwards, Gillian, et al. (1993) "The Pharmacology of ATP–Sensitive Potassium Channels", *Annu. Rev. Pharmacol. Toxicol.* 33:597–637.

*Primary Examiner*—Eggerton A. Campbell
*Attorney, Agent, or Firm*—Towsend and Townsend and Crew LLP

[57] ABSTRACT

This invention relates to DNA and protein compositions useful in the diagnosis and treatment of diabetes, heart disease and skeletal muscle disease. More specifically, this invention relates to DNA and protein compositions for ATP-sensitive potassium channel proteins, and methods of using these compositions.

9 Claims, No Drawings

DNA ENCODING ATP-SENSITIVE POTASSIUM CHANNEL GENES

This application is a continuation-in-part of co-pending U.S. patent application Ser. No. 08/288,510 filed Aug. 10, 1994, which is a continuation-in-part of U.S. patent application Ser. No. 08/193,372 filed Feb. 8, 1994 abandoned. The above applications are hereby incorporated by reference.

This invention was made with Government Support under Grant number NS28504 awarded by the National Institutes of Health. The Government has certain rights to this invention.

FIELD OF THE INVENTION

This invention relates to DNA and protein compositions useful in the diagnosis and treatment of diabetes, heart disease and skeletal muscle disease. More specifically, this invention relates to DNA and protein compositions for ATP-sensitive potassium channel proteins, and methods of using these compositions.

BACKGROUND OF THE INVENTION

The concentration of potassium ions is maintained at a relatively high concentration intracellularly, primarily by the action of a sodium-potassium pump present in the cell membrane. The transport of potassium across the cell membrane is also regulated by a variety of potassium channel proteins which are present in the cell membranes of various tissues. One type of potassium channel is inhibited by ATP and has been termed the ATP-sensitive potassium channel. (See Ashcroft, S. M. (1988) *Ann Rev. Neurosci.* 11:97–118 and Edwards, G., et al. (1993) *Ann. Rev. Pharmacol. Toxicol.* 33:597–637 for a description of ATP-sensitive potassium ion channels.)

ATP-sensitive potassium channels are inhibited by ATP. The physiology, pharmacology, and tissue distribution of the ATP-sensitive potassium channels has been extensively studied by the membrane patch-clamp technique (see Ashcroft, S. M., supra). Potassium channels are known to be present in cardiac and skeletal muscle as well as in the insulin-secreting β-cells of the pancreas. In addition, there is evidence that ATP-sensitive potassium channels are also present in smooth muscle and in neurons.

The ATP-sensitive potassium channel has important physiological functions in the pancreas. The ATP-sensitive potassium channel plays a key role in mediating glucose-stimulated insulin release from pancreatic β-cells. Modulation of the pancreatic ATP-sensitive potassium channel is also important in treatment of diabetes. For example, sulfonylurea drugs, such as glyburide, that are used in the treatment of non-insulin dependent diabetes are known to stimulate insulin secretion by inhibiting the opening of the ATP-sensitive potassium channel.

The ATP-sensitive potassium channel is also important in the physiology and pathophysiology of the heart. For instance, activation of the ATP-sensitive potassium channel in anoxia appears to be responsible for shortening the ventricular action potential and reducing heart muscle contraction. Activation of the potassium channel also increases the threshold for electrical excitation thereby slowing pacemaker activity. The ATP-sensitive potassium channel appears to be the target for drugs used as potassium channel openers in heart muscle.

In addition to its role in cardiac muscle, the ATP-sensitive potassium channel is also involved in regulation of potassium ion transport in skeletal muscle. Potassium channel openers that target the ATP-sensitive potassium channel may be useful in skeletal muscle diseases such as myotonia congentia and hyperkalemic paralysis (see Edwards, G., et al., supra).

Many of the potential uses of ATP-sensitive potassium channel proteins require isolation of the proteins or isolation of DNA encoding the proteins. The sequence of the potassium channel proteins and the genes encoding them have not been described in the prior art. Isolation of ATP-sensitive potassium channel proteins and DNA encoding these proteins facilitates the design and selection of improved potassium channel inhibitors and potassium channel openers useful in treatment of diabetes, heart disease, and skeletal muscle disease. Isolation of these proteins and genes also allows for development of in vitro diagnostic methods for detection and diagnosis of disorders involving the ATP-sensitive potassium channel. These and other needs are addressed by the present invention.

SUMMARY OF THE INVENTION

The present invention provides for isolated ATP-sensitive potassium channel proteins. These proteins specifically bind to antibodies generated against an immunogen which is a protein of Seq. ID No. 2. Preferably, these ATP-sensitive potassium channel proteins are of human origin. An example of a human ATP-sensitive potassium channel protein is the protein of Seq. ID No. 2. The ATP-sensitive potassium channel proteins may also be of non-human origin, for example, of rat origin. An example of a rat ATP-sensitive potassium channel protein is the protein of Seq. ID No. 4. The ATP-sensitive potassium channel proteins can be recombinantly produced and can be full-length.

In addition to providing for ATP-sensitive potassium channel proteins, the present invention also provides for isolated nucleic acids encoding these proteins. Thus, the invention provides for nucleic acids which encode the ATP-sensitive potassium channel proteins described above. These nucleic acids can selectively hybridize to a nucleic acid encoding a human heart ATP-sensitive potassium protein of Seq. ID No. 1 in the presence of a genomic library under hybridization wash conditions of 50% formamide at 42° C. Preferably these nucleic acids are of human origin. An example of a nucleic acid encoding a human ATP-sensitive potassium channel protein is the nucleic acid of Seq. ID No. 1. These nucleic acids can also be of non-human origin, for example, of rat origin. An example of a nucleic acid encoding a rat ATP-sensitive potassium channel protein is the nucleic acid of Seq. ID No. 3.

The invention further provides for host cells stably transfected with nucleic acids that encode ATP-sensitive potassium channel proteins. For example, host cells may be transfected with a nucleic acid of Seq. ID No. 1 or Seq. ID No. 3.

In addition to providing for host cells stably transfected with nucleic acids encoding ATP-sensitive potassium channel proteins, this invention also uses these transfected host cells to detect compounds that are capable of inhibiting or that are capable of accelerating the movement of potassium through ATP-sensitive potassium channels in the cell membrane. In these methods, the electrical potential is measured across a cell membrane of the transfected host cell. Preferably, the transfected host cell is a eukaryotic cell. Examples of such cells are HEK293 and BHK21 cells. An example of a compound that is detected in this method is pinacidil.

The invention further provides for nucleic acid probes that are capable of selectively hybridizing to a nucleic acid encoding an ATP-sensitive potassium channel protein. For example, the nucleic acid probe can be the nucleic acid of Seq. ID No. 1 or the nucleic acid of Seq. ID No. 3. As an additional example, the nucleic acid probe can be capable of hybridizing to a nucleic acid encoding the protein of Seq. ID No. 2 or Seq. ID No. 4. These nucleic acid probes can be used to measure or detect nucleic acids encoding ATP-sensitive potassium channel proteins. The probes are incubated with a biological sample to form a hybrid of the probe with complementary nucleic acid sequences present in the sample. The extent of hybridization of the probe to these complementary nucleic acid sequences is then determined. Preferably the biological sample is human.

The invention further provides for antibodies specifically immunoreactive with the protein of Seq. ID No. 2. Methods of measuring or detecting ATP-sensitive potassium channel proteins and antibodies reactive with these proteins are also provided. ATP-sensitive potassium channel proteins can be detected by incubating a biological sample with a binding agent having an affinity for these proteins to form a binding agent:ATP-sensitive potassium channel protein complex and detecting the complex. Preferably, the binding agent is an antibody and the biological sample is human.

Antibodies reactive to ATP-sensitive potassium channel proteins present in biological samples can be detected by incubating a recombinant or isolated ATP-sensitive potassium channel protein with a biological sample to form an antibody:ATP-sensitive potassium channel protein complex, and detecting the complex. Preferably, the biological sample is human.

DEFINITIONS

Abbreviations for the twenty naturally occurring amino acids follow conventional usage. In the polypeptide notation used herein, the left-hand direction is the amino terminal direction and the right-hand direction is the carboxy-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

The phrase "isolated" or "substantially pure" when referring to nucleic acid sequences encoding ATP-sensitive potassium channel proteins refers to isolated nucleic acids that do not encode proteins or peptides other than ATP-sensitive potassium channel proteins or peptides.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes both extra-chromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as the nucleic acid sequence of Seq. ID No. 2, or may comprise a complete cDNA or gene sequence.

Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the human heart ATP-sensitive potassium channel protein disclosed herein.

As applied to polypeptides, the terms "substantial identity" or "substantial sequence identity" mean that two peptide sequences, when optimally aligned, such as by the programs GAP or BESTFIT using default gap weights, share at least 70 percent sequence identity, preferably at least 80 percent sequence identity, more preferably at least 90 percent sequence identity, and most preferably at least 95 percent amino acid identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to an ATP-sensitive potassium channel peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the human heart ATP-sensitive potassium channel protein immunogen with the amino acid sequence depicted in Seq. ID No. 2 can be selected to obtain antibodies specifically immunoreactive with ATP-sensitive potassium channel proteins and not with other proteins. These antibodies recognize proteins homologous to the human heart ATP-sensitive potassium channel protein. Homologous proteins encompass the family of ATP-sensitive potassium channel proteins, but do not include other potassium channel proteins which are not inhibited by ATP. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "binding agent:ATP-sensitive potassium channel protein complex", as used herein, refers to a complex of a binding agent and an ATP-sensitive potassium channel protein that is formed by specific binding of the binding agent to the ATP-sensitive potassium channel protein. Specific binding of the binding agent means that the binding agent has a specific binding site that recognizes a site on the ATP-sensitive potassium channel protein. For example, antibodies raised to an ATP-sensitive potassium channel protein and recognizing an epitope on the ATP-sensitive potassium channel protein are capable of forming a binding agent:ATP-sensitive potassium channel protein complex by specific binding. Typically, the formation of a binding agent:ATP-sensitive potassium channel protein complex allows the measurement of ATP-sensitive potassium channel protein in a mixture of other proteins and biologics. The term "antibody:ATP-sensitive potassium channel protein complex" refers to a binding agent:ATP-sensitive potassium channel protein complex in which the binding agent is an antibody.

"Biological sample" as used herein refers to any sample obtained from a living organism or from an organism that has died. Examples of biological samples include body fluids and tissue specimens.

DETAILED DESCRIPTION

This invention provides for isolated ATP-sensitive potassium channel proteins and for isolated nucleic acids encoding these proteins. These isolated DNA and protein compositions can be used in a number of applications. For instance, they can be used for the design and selection of potassium channel openers and inhibitors that act on the ATP-sensitive potassium channel. These compositions can also be used in in vitro diagnostic methods for the detection and diagnosis of diseases, such as diabetes and heart disease, which involves ATP-sensitive potassium channels. Compositions and methods for using the DNA and protein sequences of the ATP-sensitive potassium channel proteins are described below.

A. ATP-sensitive Potassium Channel Proteins

As described above, ATP-sensitive potassium channel proteins are known to be active in heart, skeletal muscle and pancreatic β-cells. In addition, there is evidence that these proteins are present in neurons and smooth muscle tissue as well.

The ATP-sensitive potassium channel proteins present in different tissues appear to be the product of different genes. For example, the pancreatic β-cell ATP-sensitive potassium channel protein is a different gene product from the heart ATP-sensitive potassium channel protein. Thus, the ATP-sensitive potassium channel proteins represent a family of highly homologous proteins with the same functional characteristics. The predicted amino acid sequence of the human heart ATP-sensitive potassium channel protein and the rat heart ATP-sensitive potassium channel protein is shown as Seq. ID No. 2 and Seq. ID No. 4, respectively. The predicted amino acid sequence of the rat pancreatic β-cell ATP-sensitive potassium channel protein is shown as Seq. ID No. 13, and a full-length or nearly full-length predicted amino acid sequence of the human pancreatic β-cell ATP-sensitive potassium channel protein is shown as Seq. ID No. 15.

The amino acid sequences listed for the rat and human heart ATP-sensitive potassium channel proteins are full-length sequences, as is the amino acid sequence listed for the rat β-cell channel protein. The human β-cell ATP-sensitive potassium channel protein is a full-length sequence or a nearly full-length sequence. When the initiator methione designated in the cDNA sequence of Seq. ID No. 14 is used in a heterologous expression system, functional ATP channel proteins with the amino acid sequence of Seq. ID No. 15 are produced.

The percent amino acid identity of these proteins was determined by the GAP computer program (version 7.3.1, Genetics Computer Group, 575 Science Drive, Madison, Wis.). The Needleman and Wunsch homology alignment algorithm was used with the default settings. Using this procedure, there is 95.95% amino acid identity between the amino acid sequences for the rat and human heart ATP-sensitive potassium channel proteins. By comparison, there is 98.2% amino acid identity between the amino acid sequences for the rat and human pancreatic β-cell ATP-sensitive potassium channel proteins. In contrast, there is 72.3% amino acid identity when the rat heart ATP-sensitive potassium channel protein sequence is compared to that of the rat pancreatic β-cell ATP-sensitive potassium channel protein. Lastly, there is 74.9% amino acid identity between the amino acid sequences of the human heart ATP-sensitive potassium channel protein and the human pancreatic β-cell ATP-sensitive potassium channel protein.

The term "ATP-sensitive potassium channel protein" refers to a family of proteins that form a potassium channel in the cell membrane which is inhibited by high intracellular concentrations of ATP. ATP-sensitive potassium channel proteins are known to be present and active in certain vertebrate tissues such as heart, skeletal muscle and the pancreas. The physiological and pharmacological characteristics of ATP-sensitive potassium channels have been characterized by the membrane patch-clamp technique (see Hamil, O. P., et al. (1981) Pflugers Arch. 351:85–100. Accordingly, the proteins are defined by their functional characteristics when present in active form in the cell membrane. For instance, ATP-sensitive potassium channels are inhibited by ATP with a half maximal inhibition in the range of 10–100 μM. They have a unitary conductance of from 40–80 pS when measured under high symmetrical potassium concentrations, and are calcium- and voltage-independent and potassium selective. They are inhibited by agents such as tolbutamide and glyburide. For a detailed description of the properties of ATP-sensitive potassium channels, see Ashcroft, F. M. supra and Edwards, G., et al. supra. ATP-sensitive potassium channel proteins typically show substantial sequence identity (as defined above) to the amino acid sequence of the human heart ATP-sensitive potassium channel protein as depicted in Seq. ID No. 2. ATP-sensitive potassium channel proteins from different tissues and from different mammalian species are all specifically immunoreactive with antibodies raised to the human heart ATP-sensitive potassium channel protein described herein and consisting of the amino acid sequence of Seq. ID. No. 2.

An ATP-sensitive potassium channel protein that specifically binds to or that is specifically immunoreactive to an antibody generated against a defined immunogen, such as an immunogen consisting of the amino acid sequence of Seq. ID No. 2, is determined in an immunoassay. The immunoassay uses a polyclonal antiserum which was raised to the protein of Seq. ID No. 2. This antiserum is selected to have low crossreactivity against other (non-ATP-sensitive) potassium channel proteins and any such crossreactivity is removed by immnuoabsorbtion prior to use in the immunoassay.

In order to produce antisera for use in an immunoassay, the protein of Seq. ID No. 2 is isolated as described herein. For example, recombinant protein is produced in a mammalian cell line. An inbred strain of mice such as balb/c is immunized with the protein of Seq. ID No. 2 using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. For instance, the peptides of Seq. ID Nos. 10 and 11 may be used. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-ATP-sensitive potassium channel proteins, using a competitive binding immunoassay such as the one described in Harlow and Lane, supra, at pages 570–573. Three non-ATP sensitive potassium channel proteins are used in this determination: the IRK protein (Kubo, et al. (1993) *Nature* 362:127), the G-IRK protein (Kubo, et al. (1993) *Nature* 364:802) and the ROM-K protein (Ho, et al. (1993) *Nature* 362:127. These non-ATP sensitive potassium channel proteins can be produced as recombinant proteins and isolated using standard molecular biology and protein chemistry techniques as described herein.

Immunoassays in the competitive binding format can be used for the crossreactivity determinations. For example, the protein of Seq. ID No. 2 can be immobilized to a solid support. Proteins added to the assay compete with the binding of the antisera to the immobilized antigen. The ability of the above proteins to compete with the binding of the antisera to the immobilized protein is compared to the protein of Seq. ID No. 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (the ATP-sensitive potassium channel protein of Seq. ID No. 2). In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein of Seq. ID No. 2 that is required, then the second protein is said to specifically bind to an antibody generated to an immunogen consisting of the protein of Seq. ID No. 2.

It is understood that ATP-sensitive potassium channel proteins refer to a family of homologous proteins that are encoded by two or more genes. For a particular gene product, such as the human heart ATP-sensitive potassium channel protein, the term refers not only to the amino acid sequences disclosed herein, but also to other proteins that are allelic, non-allelic or species variants. It also understood that the term "ATP-sensitive potassium channel proteins" includes nonnatural mutations introduced by deliberate mutation using conventional recombinant technology such as single site mutation or by excising short sections of DNA encoding ATP-sensitive potassium channel proteins or by substituting new amino acids or adding new amino acids. Such minor alterations must substantially maintain the immunoidentity of the original molecule and/or its biological activity. Thus, these alterations include proteins that are specifically immunoreactive with a designated naturally occurring ATP-sensitive potassium channel protein, for example, the human heart protein shown in Seq. ID No. 2. The biological properties of the altered proteins can be determined by expressing the protein in an appropriate cell line and using the membrane patch-clamp technique to determine the function of the ATP-sensitive potassium channel in a membrane patch (see example 4, herein). Particular protein modifications considered minor would include substitution of amino acids of similar chemical properties, e.g., glutamic acid for aspartic acid or glutamine for asparagine. By aligning a protein optimally with the protein of Seq. ID No. 2 and by using the conventional immunoassays described herein to determine immunoidentity, or by using patch-clamp membrane techniques to determine biological activity, one can readily determine the protein compositions of the invention.

ATP-sensitive potassium channel proteins designated by their tissue of origin refer to the gene-product from this family that is predominantly expressed in that tissue. For instance, the term "heart ATP-sensitive potassium channel protein" refers to the ATP-sensitive potassium channel protein that is expressed in heart tissue. As another example, the term "pancreatic β-cell ATP-sensitive potassium channel protein" refers to the ATP-sensitive protein that is expressed in the pancreatic β-cell. Since ATP-sensitive potassium channel proteins represent a family of homologous proteins, the proteins expressed in different tissues can be the product of different genes in the family.

B. Nucleic Acids Encoding ATP—sensitive Potassium Channel Proteins

This invention relates to isolated nucleic acid sequences encoding ATP-sensitive potassium channel proteins. The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

The nucleic acid sequences of the invention are typically identical to or show substantial sequence identity (determined as described above) to the nucleic acid sequence of SEQ ID. No. 1. Nucleic acids encoding mammalian ATP-sensitive potassium channel proteins will typically hybridize to the nucleic acid sequence of Seq. ID No. 1 under stringent conditions. For example, nucleic acids encoding ATP-sensitive potassium channel proteins will hybridize to the nucleic acid of sequence ID No. 1 under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60°0 C. As other factors may significantly affect the stringency of hybridization, including, among others, base composition and size of the complementary strands, the presence of organic solvents and the extent of base mismatching, the combination of parameters is more important than the absolute measure of any one.

Techniques for nucleic acid manipulation of genes encoding the ATP-sensitive potassium channel proteins such as subcloning nucleic acid sequences encoding polypeptides into expression vectors, labelling probes, DNA hybridization, and the like are described generally in Sambrook, et al.. *Molecular Cloning—A Laboratory Manual* (2nd Ed.), Vol. 1–3, Cold Spring Harbor Laboratory, Cold Spring Harbor, N.Y. 1989, which is incorporated herein by reference. This manual is hereinafter referred to as "Sambrook, et al."

There are various methods of isolating the DNA sequences encoding ATP-sensitive potassium channel proteins. For example, DNA is isolated from a genomic or cDNA library using labelled oligonucleotide probes having sequences complementary to the sequences disclosed herein (Seq. ID Nos. 1, 3, 8, 12 and 14). For example, full-length probes may be used, or oligonucleotide probes may also be generated by comparison of the sequences of Seq. ID Nos. 1, 3, 8, 12 and 14. Such probes can be used directly in hybridization assays to isolate DNA encoding ATP-sensitive potassium channel proteins. Alternatively probes can be designed for use in amplification techniques such as PCR, and DNA encoding ATP-sensitive potassium channel proteins may be isolated by using methods such as PCR (see below).

To prepare a cDNA library, MRNA is isolated from tissue such as heart or pancreas which expresses an ATP-sensitive potassium channel protein. cDNA is prepared from the mRNA and ligated into a recombinant vector. The vector is transfected into a recombinant host for propagation, screening and cloning. Methods for making and screening cDNA libraries are well known. See Gubler, U. and Hoffman, B . J. *Gene* 25:263–269, 1983 and Sambrook, et al.

For a genomic library, the DNA is extracted from tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science*, 196:180–182 (1977). Colony hybridization is carried out as generally described in M. Grunstein et al. *Proc. Natl. Acad. Sci. USA.*, 72:3961–3965 (1975).

DNA encoding an ATP-sensitive potassium channel protein is identified in either cDNA or genomic libraries by its ability to hybridize with nucleic acid probes, for example on Southern blots, and these DNA regions are isolated by standard methods familiar to those of skill in the art. See Sambrook, et al.

Various methods of amplifying target sequences, such as the polymerase chain reaction, can also be used to prepare DNA encoding ATP-sensitive potassium channel protein. Polymerase chain reaction (PCR) technology is used to amplify such nucleic acid sequences directly from mRNA, from cDNA, and from genomic libraries or cDNA libraries. The isolated sequences encoding ATP-sensitive potassium channel protein may also be used as templates for PCR amplification.

In PCR techniques, oligonucleotide primers complementary to the two 3' borders of the DNA region to be amplified are synthesized. The polymerase chain reaction is then carried out using the two primers. See *PCR Protocols: A Guide to Methods and Applications*. (Innis, M, Gelfand, D., Sninsky, J. and White, T., eds.), Academic Press, San Diego (1990). Primers can be selected to amplify the entire regions encoding a full-length ATP-sensitive potassium channel protein or to amplify smaller DNA segments as desired.

PCR can be used in a variety of protocols to isolate cDNA's encoding the ATP-sensitive potassium channel proteins. In these protocols, appropriate primers and probes for amplifying DNA encoding ATP-sensitive potassium channel proteins are generated from analysis of the DNA sequences listed herein. For example, the oligonucleotides of Seq. ID Nos. 5 and 6 can be used in a PCR protocol as described in example 2 herein to amplify regions of DNA's encoding potassium channel proteins. Once such regions are PCR-amplified, they can be sequenced and oligonucleotide probes can be prepared from sequence obtained. These probes can then be used to isolate DNA's encoding ATP-sensitive potassium channel proteins, similar to the procedure used in example 2 herein. ATP-sensitive potassium channel proteins can be isolated from a variety of different tissues using this procedure. Other oligonucleotide probes in addition to those of Seq. ID No. 5 and 6 and which are obtained from the sequences described herein can also be used in PCR protocols to isolate cDNA's encoding the ATP-sensitive potassium channel proteins.

Oligonucleotides for use as probes are chemically synthesized according to the solid phase phosphoramidite triester method first described by Beaucage, S. L. and Carruthers, M. H., 1981, *Tetrahedron Lett.*, 22(20) :1859–1862 using an automated synthesizer, as described in Needham-VanDevanter, D. R., et al., 1984, *Nucleic Acids Res.*, 12:6159–6168. Purification of oligonucleotides is by either native acrylamide gel electrophoresis or by anion-exchange HPLC as described in Pearson, J. D. and Regnier, F. E., 1983, *J. Chrom.*, 255:137–149. The sequence of the synthetic oligonucleotide can be verified using the chemical degradation method of Maxam, A. M. and Gilbert, W. 1980, in Grossman, L. and Moldave, D., eds. Academic Press, New York. *Methods in Enzymology*, 65:499–560.

Other methods known to those of skill in the art may also be used to isolate DNA encoding the ATP-sensitive potassium channel protein. See Sambrook, et al. for a description of other techniques for the isolation of DNA encoding specific protein molecules.

C. Expression of ATP-sensitive potassium channel proteins

Once DNA encoding ATP-sensitive potassium channel proteins is isolated and cloned, one can express the ATP-sensitive potassium channel proteins in a variety of recombinantly engineered cells. It is expected that those of skill in the art are knowledgeable in the numerous expression systems available for expression of DNA encoding ATP-sensitive potassium channel proteins. No attempt to describe in detail the various methods known for the expression of proteins in prokaryotes or eukaryotes is made here.

In brief summary, the expression of natural or synthetic nucleic acids encoding ATP-sensitive potassium channel proteins will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence encoding ATP-sensitive potassium channel proteins. To obtain high level expression of a cloned gene, such as those polynucleotide sequences encoding ATP-sensitive potassium channel proteins, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al. Examples of expression of ATP-sensitive potassium channel proteins in both prokaryotic and eukaryotic systems are described below.

1. Expression in Prokaryotes

A variety of procaryotic expression systems may be used to express ATP-sensitive potassium channel proteins. Examples include *E. coli*, Bacillus, Streptomyces, and the like. For example, ATP-sensitive potassium channel proteins may be expressed in *E. coli*.

It is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., 1984, *J. Bacteriol.*, 158:1018–1024 and the leftward promoter of phage lambda (PλP) as described by Herskowitz, I. and Hagen, D., 1980, *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

ATP-sensitive potassium channel proteins produced by prokaryotic cells may not necessarily fold properly. During purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from *E. coli* can be achieved following procedures described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, ATP-sensitive potassium channel proteins may be expressed in these eukaryotic systems.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene*, 8:17–24; Broach, et al., 1979, *Gene*, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, *Nature* (London), 275:104–109; and Hinnen, A., et al., 1978, *Proc. Natl. Acad. Sci. USA*, 75:1929–1933. The second procedure does not involve removal of the cell wall. Instead the cells are treated with lithium chloride or acetate and PEG and put on selective plates (Ito, H., et al., 1983, *J. Bact.*, 153:163–168).

ATP-sensitive potassium channel proteins, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding ATP-sensitive potassium channel proteins can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of ATP-sensitive potassium channel proteins are available, for instance, from the American Type Culture Collection Catalogue of Cell Lines and Hybridomas (7th edition, 1992).

Appropriate vectors for expressing ATP-sensitive potassium channel proteins in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27:353–365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, *J. Virol.* 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. *Biochemical Methods in Cell Culture and Virology*, Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

D. Purification of ATP-sensitive potassium channel proteins

The polypeptides produced by recombinant DNA technology may be purified by standard techniques well known to those of skill in the art. Recombinantly produced polypeptides can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference. For example, antibodies may be raised to the ATP-sensitive potassium channel proteins as described herein. Cell membranes are isolated from a cell line expressing the recombinant protein, the protein is extracted from the membranes and immunoprecipitated. The proteins may then be further purified by standard protein chemistry techniques as described above.

E. Assays for Biologically Active ATP-sensitive Potassium Channel Proteins and for DNA encoding Such Proteins The presence of ATP-sensitive potassium channel proteins may be measured by a variety of techniques. For example, the proteins may be measured in immunoassays as described below. In addition, biologically active ATP-sensitive potassium channel proteins or DNA encoding such proteins can be measured by the membrane patch-clamp technique (see Hamil, O. P. et al. (1981) *Pflugers Arch.* 351:85–100). In order to use this technique, DNA or cDNA encoding ATP-sensitive potassium channel proteins is first isolated, inserted into a suitable expression vector and transfected into a cell line, as described herein. Expression of recombinant ATP-sensitive proteins in an appropriate cell line results in the incorporation of the protein into the cell membrane. Cell-free membrane patches are prepared and single channel currents are measured by the membrane patch-clamp technique. (See Ashcroft, F. M., et al. supra for a review of the measurement of ATP-sensitive potassium channels by the patch-clamp technique.) An example of the use of the membrane patch-clamp technique to detect DNA encoding ATP-sensitive potassium channel proteins is described in example 4, herein.

F. Assays for Compounds that Inhibit or Open the ATP-sensitive Potassium Channel DNA encoding ATP-sensitive potassium channel proteins or recombinantly produced proteins can be used in a variety of assays to detect compounds that are inhibitors or openers of the ATP-sensitive potassium channel. For example, the membrane patch-clamp technique can be used for this purpose. Isolated DNA encoding an ATP-sensitive potassium channel protein can be inserted into an expression vector, transfected into an appropriate cell line and expressed in the cell line as described herein. Single channel currents are measured in cell free membrane patches as described above (see Ashcroft, F. M., et al. supra). Assays for compounds capable of opening the A of opening the ATP-sensitive potassium channel can be performed by application of the compounds to a bath solution including ATP as described by Fan, Z., et al. (1993) *Pflugers Arch.* 415:387–394. (See example 5 herein for an illustration of the use of the patch-clamp technique to measure an ATP-sensitive potassium channel opener.) Assays for compounds that are inhibitors of the ATP-sensitive potassium channel can be measured under similar conditions (see Ashcroft, F. M., supra).

In addition to assaying for compounds with unknown activity, the compositions of the invention can also be used to determine the concentration of known ATP-sensitive potassium channel openers and inhibitors. For example, the membrane patch-clamp technique can be used with transfected cell lines as described above. However, different concentrations of known ATP-sensitive potassium channel openers or inhibitors can be applied under designated conditions. Concentrations of biologically active compounds can be expressed as activity units under standardized conditions or can by expressed in mass of the compound by reference to a standard preparation of the compound. A threshold level for opening or inhibiting the ATP-sensitive potassium channel is used. For instance, the patch-clamp measurement conditions and the threshold level as described in Fan, Z. et al., supra, could be used. The determination of the concentration of pinacidil, an ATP-sensitive potassium channel opener is illustrated in example 5, herein. Other potassium channel openers may also be measured by this method.

The concentration of potassium channel inhibitors such as sulfonylurea drugs can also be measured by similar methods. For instance, the assay described in example 5 can readily be modified to measure a compound that inhibits rather than activates the ATP-sensitive potassium channel. Examples of ATP-sensitive potassium channel inhibitors include glyburide and tolbutamide (both obtained from Upjohn, Kalamazoo, Mich., U.S.A.). Examples of ATP-sensitive potassium channel openers include pinacidil (Upjohn), diazide, nicorandil, cromakalim, and a variety of other compounds. (See Edwards, G., et al., supra for a discussion of ATP-sensitive potassium channel openers and inhibitors.)

G. In Vitro Diagnostic Methods: Detection of Nucleic Acids Encoding ATP-sensitive Potassium Channel Proteins and Detection of ATP-sensitive Potassium Channel Proteins by Immunoassay The present invention provides methods for detecting DNA or RNA encoding ATP-sensitive potassium channel proteins and for measuring the proteins by immunoassay techniques. These methods are useful for two general purposes. First, assays for detection of nucleic acids encoding ATP-sensitive potassium channel proteins are useful for the isolation of these nucleic acids from a variety of vertebrate species according to the methods described in section (B) above and by use of the nucleic acid hybridization assays described below. The immunoassays described below may be useful for isolation of nucleic acids encoding ATP-sensitive potassium channel proteins by expression cloning methods (see section (B) above and Sambrook, et al.).

The nucleic acid hybridization assays and the immunoassays described below are also useful as in vitro diagnostic assays for disorders in which alterations in ATP-sensitive potassium channel proteins play a role. These diseases include diabetes, heart disease, and certain skeletal muscle disorders.

1. Nucleic Acid Hybridization Assays

A variety of methods for specific DNA and RNA measurement using nucleic acid hybridization techniques are known to those of skill in the art. See Sambrook, et al. For example, one method for evaluating the presence or absence of DNA encoding ATP-sensitive potassium channel proteins in a sample involves a Southern transfer. Briefly, the digested genomic DNA is run on agarose slab gels in buffer and transferred to membranes. Hybridization is carried out using the nucleic acid probes discussed above. As described above, nucleic acid probes are designed based on the nucleic acid sequences encoding the human heart and rat heart ATP-sensitive potassium channel proteins or the pancreatic β-cell protein. (See Seq. ID. Nos. 1, 3, 8, 12 and 14.) The probes can be full length or less than the full length of the nucleic acid sequence encoding the potassium channel protein. Shorter probes are empirically tested for specificity. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA encoding ATP-sensitive potassium channel proteins.

Similarly, a Northern transfer may be used for the detection of mRNA encoding ATP-sensitive potassium channel proteins. In brief, the mRNA is isolated from a given cell sample using an acid guanidinium-phenol-chloroform extraction method. The MRNA is then electrophoresed to separate the mRNA species and the MRNA is transferred from the gel to a nitrocellulose membrane. As with the Southern blots, labeled probes are used to identify the presence or absence of ATP-sensitive potassium channel proteins.

A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985; Gall and Pardue (1969), *Proc. Natl. Acad. Sci., U.S.A.*, 63:378–383; and John, Burnsteil and Jones (1969) *Nature*, 223:58–587.

For example, sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3H$, $^{125}I$, $^{35}S$, $^{14}C$, or $^{32}P$-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding an ATP-sensitive potassium channel protein is in situ hybridization. In situ hybridization assays are well known and are generally described in Angerer, et al., *Methods Enzymol.*, 152:649–660 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to ATP-sensitive potassium channel proteins. The probes are preferably labelled with radioisotopes or fluorescent reporters.

2. Production of Antibodies and Development of Immunoassays

In addition to detecting expression of ATP-sensitive potassium channel proteins by nucleic acid hybridization, one can also use immunoassays to detect the proteins. Immunoassays can be used to qualitatively or quantitatively analyze for the proteins. A general overview of the applicable technology can be found in Harlow and Lane, *Antibodies: A Laboratory Manual*, Cold Spring Harbor Pubs., New York (1988), incorporated herein by reference.

a. Antibody Production

A number of immunogens may be used to produce antibodies specifically reactive with ATP-sensitive potassium channel proteins. Recombinant protein is the preferred immunogen for the production of monoclonal or polyclonal antibodies. Naturally occurring protein may also be used either in pure or impure form. Synthetic peptides made using the human heart or rat heart ATP-sensitive potassium channel protein sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the ATP-sensitive potassium channel protein. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Methods of production of synthetic peptides are known to those of skill in the art. Briefly, the predicted immunogenic regions of the ATP-sensitive potassium channel protein sequences described herein are identified. Peptides preferably at least 10 amino acids in length are synthesized corresponding to these regions and the peptides are conjugated to larger protein molecules for subsequent immunization. Preferably, peptide sequences corresponding to unique regions of an ATP-sensitive potassium channel protein are used to generate antibodies specifically immunoreactive with the potassium channel proteins. Examples of such peptides are depicted in Seq. ID Nos. 10 and 11. Production of monoclonal or polyclonal antibodies is then carried out as described above.

b. Immunoassays

A particular protein can be measured by a variety of immunoassay methods. For a review of immunological and immunoassay procedures in general, see *Basic and Clinical Immunology* 7th Edition (D. Stites and A. Terr ed.) 1991. Moreover, the immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, Antibodies, *A Laboratory Manual*, supra, each of which is incorporated herein by reference.

Immunoassays for measurement of ATP-sensitive potassium channel proteins can be performed by a variety of methods known to those skilled in the art. In brief, immunoassays to measure the protein can be either competitive or noncompetitive binding assays. In competitive binding assays, the sample analyte competes with a labeled analyte for specific binding sites on a capture agent bound to a solid surface. Preferably the capture agent is an antibody specifically reactive with ATP-sensitive potassium channel proteins produced as described above. The concentration of labeled analyte bound to the capture agent is inversely proportional to the amount of free analyte present in the sample.

In a competitive binding immunoassay, the ATP-sensitive potassium channel protein present in the sample competes with labelled protein for binding to a specific binding agent, for example, an antibody specifically reactive with the ATP-sensitive potassium channel protein. The binding agent may be bound to a solid surface to effect separation of bound labelled protein from the unbound labelled protein. Alternately, the competitive binding assay may be conducted in liquid phase and any of a variety of techniques known in the art may be used to separate the bound labelled protein from the unbound labelled protein. Following separation, the amount of bound labeled protein is determined. The amount of protein present in the sample is inversely proportional to the amount of labelled protein binding.

Alternatively, a homogenous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the protein.

ATP-sensitive potassium channel proteins may also be determined by a variety of noncompetitive immunoassay methods. For example, a two-site, solid phase sandwich immunoassay is used. In this type of assay, a binding agent for the protein, for example an antibody, is attached to a solid phase. A second protein binding agent, which may also be an antibody, and which binds the protein at a different site, is labelled. After binding at both sites on the protein has occurred, the unbound labelled binding agent is removed and the amount of labelled binding agent bound to the solid phase is measured. The amount of labelled binding agent bound is directly proportional to the amount of protein in the sample.

Western blot analysis can also be done to determine the presence of ATP-sensitive potassium channel proteins in a sample. Electrophoresis is carried out, for example, on a tissue sample suspected of containing the protein. Following electrophoresis to separate the proteins, and transfer of the proteins to a suitable solid support such as a nitrocellulose filter, the solid support is then incubated with an antibody reactive with the protein. This antibody may be labelled, or alternatively may be it may be detected by subsequent incubation with a second labelled antibody that binds the primary antibody.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3$H, $^{125}$I, $^{35}$S, $^{14}$C, or $^{32}$P was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see *Basic and Clinical Immunology* 7th Edition (D. Stites and A. Terr ed.) supra, *Enzyme Immunoassay*, E. T. Maggio, ed., supra, and Harlow and Lane, *Antibodies, A Laboratory Manual*, supra.

In brief, immunoassays to measure antisera reactive with ATP-sensitive potassium channel proteins can be either competitive or noncompetitive binding assays. In competitive binding assays, the sample analyte competes with a labeled analyte for specific binding sites on a capture agent bound to a solid surface. Preferably the capture agent is a purified recombinant ATP-sensitive potassium channel protein produced as described above. Other sources of ATP-sensitive potassium channel proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of ATP-sensitive potassium channel proteins.

This invention also embraces kits for detecting the presence of ATP-sensitive potassium channel proteins in tissue or blood samples which comprise a container containing antibodies selectively immunoreactive to the protein and instructional material for performing the test. The kit may also contain other components such as ATP-sensitive potassium channel proteins, controls, buffer solutions, and secondary antibodies. Kits for detecting antibodies to ATP-sensitive potassium channel proteins comprise a container containing an ATP-sensitive potassium channel protein, instructional material and may comprise other materials such as secondary antibodies and labels as described herein.

This invention further embraces diagnostic kits for detecting DNA or RNA encoding ATP-sensitive potassium channel proteins in tissue or blood samples which comprise nucleic probes as described herein and instructional material. The kit may also contain additional components such as labeled compounds, as described herein, for identification of duplexed nucleic acids.

EXAMPLES

Example 1

Isolation of a cDNA encoding human heart ATP-sensitive potassium channel protein The full length coding sequence of a cDNA encoding the human heart ATP-sensitive potassium channel protein (Seq. ID No. 2) is radiolabeled by random priming and used as a hybridization probe to screen a human heart CDNA library under hybridization conditions of 1M NaCl, 1% SDS and 50% formamide at 42° C. Hybridization wash conditions are 55° C., 0.1×SSC and 0.5% SDS. Positively hybridizing clones are purified and the nucleotide and predicted amino acid sequences are determined.

Example 2

Isolation of cDNA molecules encoding rat pancreatic β-cell ATP-sensitive potassium channel protein An oligonucleotide (20mer) directed to a unique region of the cDNA encoding the rat heart ATP-sensitive potassium channel protein was used together with a second downstream oligonucleotide sequence from the rat heart ATP-sensitive potassium channel protein in the polymerase chain reaction (PCR) on cDNA derived from a rat insulinoma cell line (RinM5F). The sequence of the 20mer from the unique sequence region is 5'-ACAGAGAAGTGTCCAGAGGG-3' (Seq. ID No. 5). The sequence of the 20mer from the second region of the rat heart protein sequence is 5'-GAGGCATAGCTTCTCATCCC-3' (Seq. ID No. 6).

One microgram of poly(A)⁺ mRNA was reverse transcribed using random primers. The reaction was terminated by heating to 100° C. for 2×10 minutes. The PCR was performed by denaturing for 30 seconds at 94° C., annealing at 53° C. for 30 seconds, and extending at 72° C. for 30 seconds, for a total of 40 cycles. The reaction product was subcloned and the nucleotide sequence was determined. Based upon this sequence, a unique oligonucleotide (34mer) was synthesized, radiolabeled and used as a hybridization probe to screen the rat pancreatic cDNA libraries. The sequence of the 34mer is 5'-CCTCTTAATCCAGTCCG-TGTTGGGGTCCATTGTC-3' (Seq. ID No. 7). Hybridization was carried out in 50% formamide at 37° C. and the hybridization wash conditions were 1×SSC at 52% C.

A cDNA clone encoding a portion of the rat pancreatic β-cell cDNA protein was isolated and sequenced using standard techniques. The cDNA sequence is shown in Seq. ID No. 8 and the predicted protein sequence is shown in Seq. ID. No. 9.

A cDNA library prepared from rat brain tissue was used to isolate a cDNA clone containing a full-length coding region for the rat pancreatic β-cell ATP-sensitive potassium channel protein. Brain tissue was used because it was known that rat brain also expressed the pancreatic β-cell form of the ATP-sensitive potassium channel protein. A radiolabeled nucleic acid probe consisting of the nucleic acid sequence shown in Seq. ID. No. 8 was used to screen the cDNA library. Hybridization was carried out in 50% formamide at 37° C. and the hybridization wash conditions were 0.1×SSC at 60% C.

A cDNA clone encoding the rat pancreatic β-cell ATP-sensitive potassium channel protein was isolated and sequenced using standard techniques. The nucleotide sequence is shown in Seq. ID No. 12 and the predicted amino acid sequence for the full-length rat pancreatic β-cell ATP-sensitive potassium channel protein is shown in Seq. ID No. 13.

Example 3

Isolation of cDNA encoding a large portion of the human pancreatic β-cell ATP-sensitive potassium channel protein A nucleic acid probe consisting of the full-length sequence of the c-DNA encoding the rat pancreatic β-cell ATP-sensitive potassium channel protein (Seq. ID No. 12) was used to isolate the cDNA encoding the human pancreatic β-cell ATP-sensitive potassium channel protein. A human pancreatic cDNA library was obtained from Clontech, Palo Alto, Calif., U.S.A. The hybridization probes were radiolabeled and used to screen the human pancreatic cDNA library. Hybridization was carried out in 50% formamide at 37° C. and the hybridization wash conditions were 0.2×SSC at 55% C. Positively hybridizing phage were purified by rescreening at reduced density.

A cDNA clone encoding a full-length or nearly full length human pancreatic β-cell ATP-sensitive potassium channel protein was isolated and sequenced using standard techniques. The nucleotide sequence is shown in Seq. ID No. 14 and the predicted amino acid sequence is shown in Seq. ID No. 15.

Example 4

An assay for DNA encoding an ATP-sensitive potassium channel protein

The presence of DNA encoding human heart ATP-sensitive potassium channel protein was determined by transfecting mammalian cells with a cDNA preparation and using the membrane patch-clamp technique (see Hamill, O. P., et al. (1981) *Pflugers Arch.* 351:85–100).

cDNA encoding an ATP-sensitive potassium channel protein from human heart tissue was isolated by using the full length coding sequence of the rat heart ATP-sensitive potassium channel protein cDNA (Seq. ID No.3) as a probe. The probe was radiolabeled by random priming and used as a hybridization probe to screen a human heart cDNA library (1M NaCL, 1% SDS, 40% formamide at 42° C.). Positively hybridizing clones were isolated. Two overlapping cDNA clones clearly encoding the human equivalent of the rat heart ATP-sensitive potassium channel protein were identified and spliced together across restriction endonuclease sites to generate a full length coding sequence. HEK293 or BHK21 tissue culture cells were grown in DMEM (Dulbecco's Modified Eagle Medium) supplemented with 10% FCS (fetal calf serum) at 37° C. in 5% $CO_2$. One day prior to transfection, $10^5$ cells were plated to a 35 mm culture dish. The following day, cells were transfected using lipofection (5 μl of Lipofectin (BRL; Gaithesburg, Md.) with 1 microgram of the plasmid pcDNAneo-rc$K_{ATP}$-1 in a total volume of 1 ml). The lipofection mixture was overlaid on the cells and incubated at 37° C. for 5 hours. The cells were then rinsed with regular media and overlaid with regular media. 18–36 hours later, transfected cells were assayed for the presence of ATP-sensitive potassium channels by electrophysiological screening.

Inside-out membrane patches were excised, as described by Hamill, O. P. et al., supra, from HEK293 or BHK21 cells which had been transfected as described above, or which had been mock transfected with water. Single channel currents were recorded using a pipette solution of 140 mM KCl, 2 mM $MgCl_2$, 10 mM HEPES (pH 7.2) and a bath solution of 140 mM KCl, 10 mM EGTA, 2 mM $CaCl_2$, 0.3 mM $MgCl_2$, 10 mM HEPES (pH 7.4); or 140 mM KCl, 5 mM EGTA, 2 mM $CaCl_2$, 2 mM $MgCl_2$, 10 mM HEPES (pH 7.4). Traces were recorded from patches containing an active ATP-sensitive potassium channel under symmetrical potassium conditions at a membrane potential of −50 mV.

ATP sensitivity of the expressed channels was determined by addition of 2 mM ATP to the bath solution (intracellular face of the patch). Application of ATP resulted in channel closure. The effect of ATP was reversed by washout of ATP from the bath solution. Under the potassium conditions described above, the single channel conductance was estimated as 70 pS from the single channel current at various potentials.

Example 5

An assay for determining the concentration of pinacidil using a recombinant ATP-sensitive potassium channel protein Pinacidil is a potent vasodilator which activates the ATP-sensitive potassium channel in cardiac muscle (see Edwards, G., et al.(1993) *Ann. Rev. Pharm.* 33: 397–637). The concentration of biologically active pinacidil is determined by transfecting and expressing the human heart ATP-sensitive potassium channel protein into a mammalian cell line and measuring the current through inside out membrane patches, using the patch clamp technique (see Hamill, O. P., et al. supra).

cDNA encoding recombinant human heart ATP-sensitive potassium channel protein is isolated as described in example 1. HEK293 or BHK21 cells are transfected as described in example 4. Membrane patches are obtained from the cells and ATP-sensitive potassium channels are determined in patch-clamp experiments as described in example 4.

Pinacidil (Upjohn, Kalamazoo, Mich., U.S.A.) is applied to the bath solution containing 2 mM ATP, but before washout of the ATP. The threshold used to detect channel openings is as described in Fan, Z., et al. (1990) *Pflugers Arch.* 415:387–394. The concentration of biologically active pinacidil is measured by the minimal concentration of the drug preparation that is effective in opening potassium channels in this system in the presence of 2 mM ATP.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

---

What is claimed is:

1. An isolated nucleic acid encoding an ATP-sensitive potassium channel protein comprising the amino acid sequence depicted by Seq. ID No. 2.

2. An isolated nucleic acid encoding an ATP-sensitive potassium channel protein and comprising a protein sequence selected from the group consisting of the protein of Seq. ID No. 2, the protein of Seq. ID No. 4, the protein of Seq. ID No. 13 and protein of Seq. ID No. 15.

3. A host cell stably transfected with the nucleic acid of claim 2.

4. An isolated deoxyribonucleic acid encoding an ATP-sensitive potassium channel protein comprising a nucleic acid sequence selected from the group of Seq. ID No. 1, Seq. ID No. 3, Seq. ID No. 12, and Seq. ID No. 14.

5. An isolated nucleic acid of claim 4 wherein the nucleotide sequence is Seq. ID No. 1 or Seq. ID No. 14.

6. An isolated nucleic acid of claim 4 wherein the nucleotide sequence is Seq. ID No. 3 or Seq. ID No. 12.

7. The nucleic acid of claim 2 wherein the encoded protein comprises the protein sequence of Seq. ID No. 2 or Seq. ID No. 4.

8. A host cell stably transfected with the nucleic acid of claim 4.

9. An isolated nucleic acid of claim 2 wherein the encoded protein comprises the protein sequence of Seq. ID No. 13 or Seq. ID No. 15.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapien ( i x ) FEATURE:
        ( A ) NAME/KEY: CDS
        ( B ) LOCATION: 1..1257

( i x ) FEATURE:
    ( A ) NAME/KEY: misc_feature
    ( B ) LOCATION: 1..1260
    ( D ) OTHER INFORMATION: /note= "cDNA encoding human heart ATP- sensitive potassium channel protein."

( x i ) SEQUENCE DESCRIPTION: SEQ ID NO:1:

```
ATG GCT GGC GAT TCT AGG AAT GCC ATG AAC CAG GAC ATG GAG ATT GGA          48
Met Ala Gly Asp Ser Arg Asn Ala Met Asn Gln Asp Met Glu Ile Gly
 1               5                  10                  15

GTC ACT CCC TGG GAC CCC AAG AAG ATT CCA AAA CAG GCC CGC GAT TAT          96
Val Thr Pro Trp Asp Pro Lys Lys Ile Pro Lys Gln Ala Arg Asp Tyr
             20                  25                  30

GTC CCC ATT GCC ACA GAC CGT ACG CGC CTG CTG GCC GAG GGC AAG AAG         144
Val Pro Ile Ala Thr Asp Arg Thr Arg Leu Leu Ala Glu Gly Lys Lys
         35                  40                  45

CCA CGC CAG CGC TAC ATG GAG AAG AGC GGC AAG TGC AAC GTG CAC CAC         192
Pro Arg Gln Arg Tyr Met Glu Lys Ser Gly Lys Cys Asn Val His His
     50                  55                  60

GGC AAC GTC CAG GAG ACC TAC CGG TAC CTG AGT GAC CTC TTC ACC ACC         240
Gly Asn Val Gln Glu Thr Tyr Arg Tyr Leu Ser Asp Leu Phe Thr Thr
 65                  70                  75                  80

CTG GTG GAC CTC AAG TGG CGC TTC AAC TTG CTC GTC TTC ACC ATG GTT         288
Leu Val Asp Leu Lys Trp Arg Phe Asn Leu Leu Val Phe Thr Met Val
                 85                  90                  95

TAC ACT GTC ACC TGG CTG TTC TTC GGC TTC ATT TGG TGG CTC ATT GCT         336
Tyr Thr Val Thr Trp Leu Phe Phe Gly Phe Ile Trp Trp Leu Ile Ala
             100                 105                 110

TAT ATC CGG GGT GAC CTG GAC CAT GTT GGC GAC CAA GAG TGG ATT CCT         384
Tyr Ile Arg Gly Asp Leu Asp His Val Gly Asp Gln Glu Trp Ile Pro
         115                 120                 125

TGT GTT GAA AAC CTC AGT GGC TTC GTG TCC GCT TTC CTG TTC TCC ATT         432
Cys Val Glu Asn Leu Ser Gly Phe Val Ser Ala Phe Leu Phe Ser Ile
     130                 135                 140

GAG ACC GAA ACA ACC ATT GGG TAT GGC TTC CGA GTC ATC ACA GAG AAG         480
Glu Thr Glu Thr Thr Ile Gly Tyr Gly Phe Arg Val Ile Thr Glu Lys
145                 150                 155                 160

TGT CCA GAG GGG ATT ATA CTC CTC TTG GTC CAG GCC ATC CTG GGC TCC         528
Cys Pro Glu Gly Ile Ile Leu Leu Leu Val Gln Ala Ile Leu Gly Ser
                165                 170                 175

ATC GTC AAT GCC TTC ATG GTG GGG TGC ATG TTT GTC AAG ATC AGC CAG         576
Ile Val Asn Ala Phe Met Val Gly Cys Met Phe Val Lys Ile Ser Gln
            180                 185                 190

CCC AAG AAG AGA GCG GAG ACC CTC ATG TTT TCC AAC AAC GCA GTC ATC         624
Pro Lys Lys Arg Ala Glu Thr Leu Met Phe Ser Asn Asn Ala Val Ile
        195                 200                 205

TCC ATG CGG GAC GAG AAG CTG TGC CTC ATG TTC CGG GTG GGC GAC CTC         672
Ser Met Arg Asp Glu Lys Leu Cys Leu Met Phe Arg Val Gly Asp Leu
    210                 215                 220

CGC AAC TCC CAC ATC GTG GAG GCC TCC ATC CGG GCC AAG CTC ATC AAG         720
Arg Asn Ser His Ile Val Glu Ala Ser Ile Arg Ala Lys Leu Ile Lys
225                 230                 235                 240

TCC CGG CAG ACC AAA GAG GGG GAG TTC ATC CCC CTG AAC CAG ACA GAC         768
Ser Arg Gln Thr Lys Glu Gly Glu Phe Ile Pro Leu Asn Gln Thr Asp
                245                 250                 255

ATC AAC GTG GGC TTT GAC ACG GGC GAC GAC CGC CTC TTC CTG GTG TCT         816
Ile Asn Val Gly Phe Asp Thr Gly Asp Asp Arg Leu Phe Leu Val Ser
            260                 265                 270

CCT CTG ATC ATC TCC CAC GAG ATC AAC GAG AAG AGC CCT TTC TGG GAG         864
Pro Leu Ile Ile Ser His Glu Ile Asn Glu Lys Ser Pro Phe Trp Glu
        275                 280                 285
```

-continued

| | | | | | | | | | | | | | | | | |
|---|---|---|---|---|---|---|---|---|---|---|---|---|---|---|---|---|
| ATG | TCT | CAG | GCT | CAG | CTG | CAT | CAG | GAA | GAG | TTT | GAA | GTT | GTG | GTC | ATT | 912 |
| Met | Ser 290 | Gln | Ala | Gln | Leu | His 295 | Gln | Glu | Glu | Phe | Glu 300 | Val | Val | Val | Ile | |
| CTA | GAA | GGG | ATG | GTG | GAA | GCC | ACA | GGC | ATG | ACC | TGC | CAA | GCC | CGG | AGC | 960 |
| Leu 305 | Glu | Gly | Met | Val 310 | Glu | Ala | Thr | Gly | Met 315 | Thr | Cys | Gln | Ala | Arg | Ser 320 | |
| TCC | TAC | ATG | GAT | ACA | GAG | GTG | CTC | TGG | GGC | CAC | CGA | TTC | ACA | CCA | GTC | 1008 |
| Ser | Tyr | Met | Asp | Thr 325 | Glu | Val | Leu | Trp | Gly 330 | His | Arg | Phe | Thr | Pro 335 | Val | |
| CTC | ACC | TTG | GAA | AAG | GGC | TTC | TAT | GAG | GTG | GAC | TAC | AAC | ACC | TTC | CAT | 1056 |
| Leu | Thr | Leu | Glu 340 | Lys | Gly | Phe | Tyr | Glu 345 | Val | Asp | Tyr | Asn | Thr 350 | Phe | His | |
| GAT | ACC | TAT | GAG | ACC | AAC | ACA | CCC | AGC | TGC | TGT | GCC | AAG | GAG | CTG | GCA | 1104 |
| Asp | Thr | Tyr 355 | Glu | Thr | Asn | Thr | Pro 360 | Ser | Cys | Cys | Ala | Lys 365 | Glu | Leu | Ala | |
| GAA | ATG | AAG | AGG | GAA | GGC | CGG | CTC | CTC | CAG | TAC | CTC | CCC | AGC | CCC | CCA | 1152 |
| Glu | Met | Lys 370 | Arg | Glu | Gly | Arg 375 | Leu | Leu | Gln | Tyr | Leu 380 | Pro | Ser | Pro | Pro | |
| CTG | CTG | GGG | CGG | TGT | GCT | GAG | GCA | GGG | CTG | GAT | GCA | GAG | GCT | GAG | CAG | 1200 |
| Leu | Leu 385 | Gly | Arg | Cys | Ala | Glu 390 | Ala | Gly | Leu | Asp | Ala 395 | Glu | Ala | Glu | Gln 400 | |
| AAT | GAA | GAA | GAT | GAG | CCC | AAG | GGG | CTG | GGT | GGG | TCC | AGG | GAG | GCC | AGG | 1248 |
| Asn | Glu | Glu | Asp | Glu 405 | Pro | Lys | Gly | Leu | Gly 410 | Gly | Ser | Arg | Glu | Ala 415 | Arg | |
| GGC | TCG | GTG | TGA | | | | | | | | | | | | | 1260 |
| Gly | Ser | Val | | | | | | | | | | | | | | |

( 2 ) INFORMATION FOR SEQ ID NO:2:

( i ) SEQUENCE CHARACTERISTICS:
        ( A ) LENGTH: 419 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ala | Gly | Asp | Ser 5 | Arg | Asn | Ala | Met | Asn 10 | Gln | Asp | Met | Glu | Ile 15 | Gly |
| Val | Thr | Pro | Trp 20 | Asp | Pro | Lys | Lys | Ile 25 | Pro | Lys | Gln | Ala | Arg 30 | Asp | Tyr |
| Val | Pro | Ile 35 | Ala | Thr | Asp | Arg | Thr 40 | Arg | Leu | Leu | Ala | Glu 45 | Gly | Lys | Lys |
| Pro | Arg 50 | Gln | Arg | Tyr | Met | Glu 55 | Lys | Ser | Gly | Lys | Cys 60 | Asn | Val | His | His |
| Gly 65 | Asn | Val | Gln | Glu | Thr 70 | Tyr | Arg | Tyr | Leu | Ser 75 | Asp | Leu | Phe | Thr | Thr 80 |
| Leu | Val | Asp | Leu | Lys 85 | Trp | Arg | Phe | Asn | Leu 90 | Leu | Val | Phe | Thr | Met 95 | Val |
| Tyr | Thr | Val | Thr 100 | Trp | Leu | Phe | Phe | Gly 105 | Phe | Ile | Trp | Trp | Leu 110 | Ile | Ala |
| Tyr | Ile | Arg 115 | Gly | Asp | Leu | Asp | His 120 | Val | Gly | Asp | Gln | Glu 125 | Trp | Ile | Pro |
| Cys | Val 130 | Glu | Asn | Leu | Ser | Gly 135 | Phe | Val | Ser | Ala | Phe 140 | Leu | Phe | Ser | Ile |
| Glu 145 | Thr | Glu | Thr | Thr | Ile 150 | Gly | Tyr | Gly | Phe | Arg 155 | Val | Ile | Thr | Glu | Lys 160 |
| Cys | Pro | Glu | Gly | Ile 165 | Ile | Leu | Leu | Leu | Val 170 | Gln | Ala | Ile | Leu | Gly 175 | Ser |

| Ile | Val | Asn | Ala | Phe | Met | Val | Gly | Cys | Met | Phe | Val | Lys | Ile | Ser | Gln |
|---|---|---|---|---|---|---|---|---|---|---|---|---|---|---|---|
| | | | 180 | | | | | 185 | | | | | 190 | | |
| Pro | Lys | Lys | Arg | Ala | Glu | Thr | Leu | Met | Phe | Ser | Asn | Asn | Ala | Val | Ile |
| | 195 | | | | | 200 | | | | | 205 | | | | |
| Ser | Met | Arg | Asp | Glu | Lys | Leu | Cys | Leu | Met | Phe | Arg | Val | Gly | Asp | Leu |
| | 210 | | | | | 215 | | | | | 220 | | | | |
| Arg | Asn | Ser | His | Ile | Val | Glu | Ala | Ser | Ile | Arg | Ala | Lys | Leu | Ile | Lys |
| 225 | | | | | 230 | | | | | 235 | | | | | 240 |
| Ser | Arg | Gln | Thr | Lys | Glu | Gly | Glu | Phe | Ile | Pro | Leu | Asn | Gln | Thr | Asp |
| | | | | 245 | | | | | 250 | | | | | 255 | |
| Ile | Asn | Val | Gly | Phe | Asp | Thr | Gly | Asp | Asp | Arg | Leu | Phe | Leu | Val | Ser |
| | | | 260 | | | | | 265 | | | | | 270 | | |
| Pro | Leu | Ile | Ile | Ser | His | Glu | Ile | Asn | Glu | Lys | Ser | Pro | Phe | Trp | Glu |
| | | 275 | | | | | 280 | | | | | 285 | | | |
| Met | Ser | Gln | Ala | Gln | Leu | His | Gln | Glu | Glu | Phe | Glu | Val | Val | Val | Ile |
| | 290 | | | | | 295 | | | | | 300 | | | | |
| Leu | Glu | Gly | Met | Val | Glu | Ala | Thr | Gly | Met | Thr | Cys | Gln | Ala | Arg | Ser |
| 305 | | | | | 310 | | | | | 315 | | | | | 320 |
| Ser | Tyr | Met | Asp | Thr | Glu | Val | Leu | Trp | Gly | His | Arg | Phe | Thr | Pro | Val |
| | | | | 325 | | | | | 330 | | | | | 335 | |
| Leu | Thr | Leu | Glu | Lys | Gly | Phe | Tyr | Glu | Val | Asp | Tyr | Asn | Thr | Phe | His |
| | | | 340 | | | | | 345 | | | | | 350 | | |
| Asp | Thr | Tyr | Glu | Thr | Asn | Thr | Pro | Ser | Cys | Cys | Ala | Lys | Glu | Leu | Ala |
| | | 355 | | | | | 360 | | | | | 365 | | | |
| Glu | Met | Lys | Arg | Glu | Gly | Arg | Leu | Leu | Gln | Tyr | Leu | Pro | Ser | Pro | Pro |
| | 370 | | | | | 375 | | | | | 380 | | | | |
| Leu | Leu | Gly | Arg | Cys | Ala | Glu | Ala | Gly | Leu | Asp | Ala | Glu | Ala | Glu | Gln |
| 385 | | | | | 390 | | | | | 395 | | | | | 400 |
| Asn | Glu | Glu | Asp | Glu | Pro | Lys | Gly | Leu | Gly | Gly | Ser | Arg | Glu | Ala | Arg |
| | | | | 405 | | | | | 410 | | | | | 415 | |
| Gly | Ser | Val | | | | | | | | | | | | | |

( 2 ) INFORMATION FOR SEQ ID NO:3:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Rat ( i x ) FEATURE:
        ( A ) NAME/KEY: misc_feature
        ( B ) LOCATION: 1..1260
        ( D ) OTHER INFORMATION: /note= "cDNA for rat heart
            ATP- sensitive potassium channel protein."

( i x ) FEATURE:
        ( A ) NAME/KEY: CDS
        ( B ) LOCATION: 1..1257

( i x ) FEATURE:
        ( A ) NAME/KEY: primer_bind
        ( B ) LOCATION: 472..491
        ( D ) OTHER INFORMATION: /note= "Sequence corresponding to
            Seq. I.D. No. 5."

( i x ) FEATURE:

( A ) NAME/KEY: primer_bind
( B ) LOCATION: 632..651
( D ) OTHER INFORMATION: /note= "Sequence complementary to Seq. I.D. No.:6"

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GCC | GGT | GAT | TCT | AGG | AAT | GCT | ATG | AAT | CAA | GAC | ATG | GAG | ATA | GGA | 48 |
| Met | Ala | Gly | Asp | Ser | Arg | Asn | Ala | Met | Asn | Gln | Asp | Met | Glu | Ile | Gly | |
| 1 | | | | 5 | | | | | 10 | | | | | 15 | | |
| GTC | ACC | TCC | CAG | GAC | CAC | AAG | AAG | ATC | CCC | AAA | CAG | GCT | CGG | GAT | TAC | 96 |
| Val | Thr | Ser | Gln | Asp | His | Lys | Lys | Ile | Pro | Lys | Gln | Ala | Arg | Asp | Tyr | |
| | | | 20 | | | | | 25 | | | | | 30 | | | |
| ATC | CCC | ATT | GCC | ACA | GAC | CGC | ACT | CGC | CTG | CTG | CCG | GAA | GGC | AAG | AAG | 144 |
| Ile | Pro | Ile | Ala | Thr | Asp | Arg | Thr | Arg | Leu | Leu | Pro | Glu | Gly | Lys | Lys | |
| | | 35 | | | | | 40 | | | | | 45 | | | | |
| CCA | CGC | CAG | CGC | TAC | ATG | GAG | AAG | ACC | GGC | AAG | TGT | AAC | GTG | CAC | CAT | 192 |
| Pro | Arg | Gln | Arg | Tyr | Met | Glu | Lys | Thr | Gly | Lys | Cys | Asn | Val | His | His | |
| | 50 | | | | | 55 | | | | | 60 | | | | | |
| GGC | AAT | GTT | CAG | GAA | ACC | TAC | CGC | TAC | CTA | AGT | GAC | CTC | TTC | ACC | ACC | 240 |
| Gly | Asn | Val | Gln | Glu | Thr | Tyr | Arg | Tyr | Leu | Ser | Asp | Leu | Phe | Thr | Thr | |
| 65 | | | | | 70 | | | | | 75 | | | | | 80 | |
| CTG | GTG | GAC | CTC | AAA | TGG | CGC | TTC | AAC | CTT | CTG | GTC | TTC | ACC | ATG | GTC | 288 |
| Leu | Val | Asp | Leu | Lys | Trp | Arg | Phe | Asn | Leu | Leu | Val | Phe | Thr | Met | Val | |
| | | | | 85 | | | | | 90 | | | | | 95 | | |
| TAC | ACC | ATT | ACT | TGG | CTA | TTC | TTT | GGC | TTC | ATC | TGG | TGG | CTC | ATT | GCT | 336 |
| Tyr | Thr | Ile | Thr | Trp | Leu | Phe | Phe | Gly | Phe | Ile | Trp | Trp | Leu | Ile | Ala | |
| | | | 100 | | | | | 105 | | | | | 110 | | | |
| TAT | GTC | CGA | GGT | GAT | CTG | GAC | CAC | GTG | GGT | GAC | CAA | GAG | TGC | ATC | CCT | 384 |
| Tyr | Val | Arg | Gly | Asp | Leu | Asp | His | Val | Gly | Asp | Gln | Glu | Cys | Ile | Pro | |
| | | 115 | | | | | 120 | | | | | 125 | | | | |
| TGT | GTT | GAA | AAC | CTT | AGT | GGC | TTT | GTG | TCT | GCT | TTC | CTG | TTC | TCC | ATT | 432 |
| Cys | Val | Glu | Asn | Leu | Ser | Gly | Phe | Val | Ser | Ala | Phe | Leu | Phe | Ser | Ile | |
| | 130 | | | | | 135 | | | | | 140 | | | | | |
| GAG | ACA | GAA | ACA | ACC | ATT | GGG | TAT | GGC | TTC | AGA | GTC | ATT | ACA | GAG | AAG | 480 |
| Glu | Thr | Glu | Thr | Thr | Ile | Gly | Tyr | Gly | Phe | Arg | Val | Ile | Thr | Glu | Lys | |
| 145 | | | | | 150 | | | | | 155 | | | | | 160 | |
| TGT | CCA | GAG | GGG | ATC | ATT | CTC | CTT | CTA | GTG | CAG | GCC | ATC | CTG | GGC | TCT | 528 |
| Cys | Pro | Glu | Gly | Ile | Ile | Leu | Leu | Leu | Val | Gln | Ala | Ile | Leu | Gly | Ser | |
| | | | | 165 | | | | | 170 | | | | | 175 | | |
| ATT | GTT | AAT | GCC | TTC | ATG | GTG | GGT | TGC | ATG | TTT | ATA | AAG | ATC | AGC | CAG | 576 |
| Ile | Val | Asn | Ala | Phe | Met | Val | Gly | Cys | Met | Phe | Ile | Lys | Ile | Ser | Gln | |
| | | | 180 | | | | | 185 | | | | | 190 | | | |
| CCA | AAG | AAG | AGA | GCA | GAG | ACC | CTC | ATG | TTC | TCC | AAC | AAT | GCT | GTC | ATC | 624 |
| Pro | Lys | Lys | Arg | Ala | Glu | Thr | Leu | Met | Phe | Ser | Asn | Asn | Ala | Val | Ile | |
| | | 195 | | | | | 200 | | | | | 205 | | | | |
| TCC | ATG | CGG | GAT | GAG | AAG | CTA | TGC | CTC | ATG | TTC | CGG | GTA | GGG | GAC | CTC | 672 |
| Ser | Met | Arg | Asp | Glu | Lys | Leu | Cys | Leu | Met | Phe | Arg | Val | Gly | Asp | Leu | |
| | 210 | | | | | 215 | | | | | 220 | | | | | |
| CGA | AAC | TCC | CAT | ATC | GTG | GAG | GCC | TTC | ATC | CGC | GCC | AAG | CTT | ATC | AAG | 720 |
| Arg | Asn | Ser | His | Ile | Val | Glu | Ala | Phe | Ile | Arg | Ala | Lys | Leu | Ile | Lys | |
| 225 | | | | | 230 | | | | | 235 | | | | | 240 | |
| TCC | CGG | CAG | ACC | AAA | GAA | GGG | GAA | TTC | ATC | CCC | TTG | AAC | CAG | ACC | GAC | 768 |
| Ser | Arg | Gln | Thr | Lys | Glu | Gly | Glu | Phe | Ile | Pro | Leu | Asn | Gln | Thr | Asp | |
| | | | | 245 | | | | | 250 | | | | | 255 | | |
| ATT | AAC | GTG | GGC | TTT | GAC | ACT | GGT | GAC | GAC | CGC | CTC | TTC | CTG | GTG | TCC | 816 |
| Ile | Asn | Val | Gly | Phe | Asp | Thr | Gly | Asp | Asp | Arg | Leu | Phe | Leu | Val | Ser | |
| | | | 260 | | | | | 265 | | | | | 270 | | | |
| CCC | CTC | TTC | ATC | TCC | CAT | GAG | ATC | AAT | GAG | AAG | AGC | CCT | TTC | TGG | GAG | 864 |
| Pro | Leu | Phe | Ile | Ser | His | Glu | Ile | Asn | Glu | Lys | Ser | Pro | Phe | Trp | Glu | |
| | | 275 | | | | | 280 | | | | | 285 | | | | |
| ATG | TCT | CGT | GCT | CAA | CTG | GAG | CAG | GAA | GAG | TTC | GAG | GTC | GTG | GTC | ATA | 912 |

```
                Met  Ser  Arg  Ala  Gln  Leu  Glu  Gln  Glu  Glu  Phe  Glu  Val  Val  Val  Ile
                     290                      295                      300

CTA  GAA  GGG  ATG  GTA  GAA  GCC  ACA  GGC  ATG  ACT  TGC  CAA  GCA  CGG  AGC              960
Leu  Glu  Gly  Met  Val  Glu  Ala  Thr  Gly  Met  Thr  Cys  Gln  Ala  Arg  Ser
305                 310                      315                      320

TCT  TAC  ATG  GAT  ACA  GAG  GTG  CTC  TGG  GGT  CAC  CGA  TTC  ACA  CCA  GTC             1008
Ser  Tyr  Met  Asp  Thr  Glu  Val  Leu  Trp  Gly  His  Arg  Phe  Thr  Pro  Val
                    325                      330                      335

CTC  ACC  TTG  GAA  AAG  GGC  TTC  TAT  GAG  GTG  GAC  TAC  AAC  ACT  TTC  CAC             1056
Leu  Thr  Leu  Glu  Lys  Gly  Phe  Tyr  Glu  Val  Asp  Tyr  Asn  Thr  Phe  His
               340                      345                      350

GAC  ACC  TAT  GAG  ACC  AAC  ACA  CCC  AGC  TGC  TGT  GCC  AAG  GAG  CTG  GCA             1104
Asp  Thr  Tyr  Glu  Thr  Asn  Thr  Pro  Ser  Cys  Cys  Ala  Lys  Glu  Leu  Ala
          355                      360                      365

GAA  ATG  AAG  AGG  AAT  GGT  GAG  CTC  CTC  CAG  TCC  TTG  CCC  AGT  CCT  CCT             1152
Glu  Met  Lys  Arg  Asn  Gly  Glu  Leu  Leu  Gln  Ser  Leu  Pro  Ser  Pro  Pro
     370                      375                      380

TTG  CTT  GGG  GGC  TGC  GCT  GAG  GCT  GAG  AAA  GAA  GCA  GAG  GCT  GAG  CAC             1200
Leu  Leu  Gly  Gly  Cys  Ala  Glu  Ala  Glu  Lys  Glu  Ala  Glu  Ala  Glu  His
385                 390                      395                      400

GAT  GAG  GAG  GAG  GAA  CCC  AAT  GGA  CTG  AGT  GTG  TCC  CGG  GCA  ACA  AGG             1248
Asp  Glu  Glu  Glu  Glu  Pro  Asn  Gly  Leu  Ser  Val  Ser  Arg  Ala  Thr  Arg
                    405                      410                      415

GGC  TCA  ATG  TGA                                                                         1260
Gly  Ser  Met
```

( 2 ) INFORMATION FOR SEQ ID NO:4:

( i ) SEQUENCE CHARACTERISTICS:
        ( A ) LENGTH: 419 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Gly  Asp  Ser  Arg  Asn  Ala  Met  Asn  Gln  Asp  Met  Glu  Ile  Gly
 1                   5                        10                       15

Val  Thr  Ser  Gln  Asp  His  Lys  Lys  Ile  Pro  Lys  Gln  Ala  Arg  Asp  Tyr
                20                       25                       30

Ile  Pro  Ile  Ala  Thr  Asp  Arg  Thr  Arg  Leu  Leu  Pro  Glu  Gly  Lys  Lys
           35                       40                       45

Pro  Arg  Gln  Arg  Tyr  Met  Glu  Lys  Thr  Gly  Lys  Cys  Asn  Val  His  His
      50                       55                       60

Gly  Asn  Val  Gln  Glu  Thr  Tyr  Arg  Tyr  Leu  Ser  Asp  Leu  Phe  Thr  Thr
 65                       70                       75                       80

Leu  Val  Asp  Leu  Lys  Trp  Arg  Phe  Asn  Leu  Leu  Val  Phe  Thr  Met  Val
                85                       90                       95

Tyr  Thr  Ile  Thr  Trp  Leu  Phe  Phe  Gly  Phe  Ile  Trp  Trp  Leu  Ile  Ala
          100                      105                      110

Tyr  Val  Arg  Gly  Asp  Leu  Asp  His  Val  Gly  Asp  Gln  Glu  Cys  Ile  Pro
          115                      120                      125

Cys  Val  Glu  Asn  Leu  Ser  Gly  Phe  Val  Ser  Ala  Phe  Leu  Phe  Ser  Ile
     130                      135                      140

Glu  Thr  Glu  Thr  Thr  Ile  Gly  Tyr  Gly  Phe  Arg  Val  Ile  Thr  Glu  Lys
145                      150                      155                      160

Cys  Pro  Glu  Gly  Ile  Ile  Leu  Leu  Leu  Val  Gln  Ala  Ile  Leu  Gly  Ser
                    165                      170                      175

Ile  Val  Asn  Ala  Phe  Met  Val  Gly  Cys  Met  Phe  Ile  Lys  Ile  Ser  Gln
```

```
            180                         185                         190
Pro Lys Lys Arg Ala Glu Thr Leu Met Phe Ser Asn Asn Ala Val Ile
        195                     200                 205

Ser Met Arg Asp Glu Lys Leu Cys Leu Met Phe Arg Val Gly Asp Leu
    210                 215                 220

Arg Asn Ser His Ile Val Glu Ala Phe Ile Arg Ala Lys Leu Ile Lys
225                 230                 235                     240

Ser Arg Gln Thr Lys Glu Gly Glu Phe Ile Pro Leu Asn Gln Thr Asp
            245                 250                     255

Ile Asn Val Gly Phe Asp Thr Gly Asp Asp Arg Leu Phe Leu Val Ser
        260                 265                 270

Pro Leu Phe Ile Ser His Glu Ile Asn Glu Lys Ser Pro Phe Trp Glu
        275                 280                 285

Met Ser Arg Ala Gln Leu Glu Gln Glu Glu Phe Glu Val Val Val Ile
    290                 295                 300

Leu Glu Gly Met Val Glu Ala Thr Gly Met Thr Cys Gln Ala Arg Ser
305                 310                 315                     320

Ser Tyr Met Asp Thr Glu Val Leu Trp Gly His Arg Phe Thr Pro Val
            325                 330                     335

Leu Thr Leu Glu Lys Gly Phe Tyr Glu Val Asp Tyr Asn Thr Phe His
            340                 345                     350

Asp Thr Tyr Glu Thr Asn Thr Pro Ser Cys Cys Ala Lys Glu Leu Ala
        355                 360                 365

Glu Met Lys Arg Asn Gly Glu Leu Leu Gln Ser Leu Pro Ser Pro Pro
    370                 375                 380

Leu Leu Gly Gly Cys Ala Glu Ala Glu Lys Glu Ala Glu Ala Glu His
385                 390                 395                     400

Asp Glu Glu Glu Glu Pro Asn Gly Leu Ser Val Ser Arg Ala Thr Arg
            405                 410                     415

Gly Ser Met
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i i ) HYPOTHETICAL: NO ( v i ) ORIGINAL SOURCE:
        ( A ) ORGANISM: Rat ( i x ) FEATURE:
        ( A ) NAME/KEY: misc_feature
        ( B ) LOCATION: 1..20
        ( D ) OTHER INFORMATION: /note= "Primer sequence that
            corresponds to nucleotides 472-491 of Seq. I.D.
            No.:3."

( x i ) SEQUENCE DESCRIPTION: SEQ ID NO:5:

ACAGAGAAGT GTCCAGAGGG                      20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (vi) ORIGINAL SOURCE:
  (A) ORGANISM: Rat (ix) FEATURE:
  (A) NAME/KEY: misc_feature
  (B) LOCATION: 1..20
  (D) OTHER INFORMATION: /note= "Primer sequence that is complementary to nucleotides 632-651 of Seq. I.D. No.:3."

(xi) SEQUENCE DESCRIPTION: SEQ ID NO:6:

GAGGCATAGC TTCTCATCCC    20

(2) INFORMATION FOR SEQ ID NO:7:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Rat (xi) SEQUENCE DESCRIPTION: SEQ ID NO:7:

CCTCTTAATC CAGTCCGTGT TGGGGTCCAT TGTC    34

(2) INFORMATION FOR SEQ ID NO:8:

(i) SEQUENCE CHARACTERISTICS:
    (A) LENGTH: 1095 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Rat (ix) FEATURE:
    (A) NAME/KEY: misc_feature
    (B) LOCATION: 1..1095
    (D) OTHER INFORMATION: /note= "Sequence of cDNA clone encoding a portion of rat pancreatic beta-cell ATP-sensitive potassium channel protein."

(ix) FEATURE:
    (A) NAME/KEY: misc_feature
    (B) LOCATION: 333..366
    (D) OTHER INFORMATION: /note= "Sequence corresponding to Seq. I.D. No.:7"

(ix) FEATURE:
    (A) NAME/KEY: CDS
    (B) LOCATION: 1..1092

(xi) SEQUENCE DESCRIPTION: SEQ ID NO:8:

```
GAT  GGG  AAG  TGT  AAC  GTC  CAC  CAC  GGC  AAC  GTG  CGG  GAG  ACG  TAC  CGA    48
Asp  Gly  Lys  Cys  Asn  Val  His  His  Gly  Asn  Val  Arg  Glu  Thr  Tyr  Arg
 1             5                        10                       15

TAC  CTG  ACG  GAC  ATC  TTC  ACC  ACC  CTG  GTG  GAC  CTA  AAG  TGG  AGA  TTC    96
Tyr  Leu  Thr  Asp  Ile  Phe  Thr  Thr  Leu  Val  Asp  Leu  Lys  Trp  Arg  Phe
              20                   25                        30
```

```
AAC CTA TTG ATC TTT GTC ATG GTC TAC ACA GTG ATG TGG CTT TTC TTT       144
Asn Leu Leu Ile Phe Val Met Val Tyr Thr Val Met Trp Leu Phe Phe
        35              40              45

GGG ATG ATC TGG TGG CTA ATT GCA TAC ATC CGG GGA GAT ATG GAC CAC       192
Gly Met Ile Trp Trp Leu Ile Ala Tyr Ile Arg Gly Asp Met Asp His
        50              55              60

ATA GAG GAC CCC CCG TGG ACT CCC TGT GTT ACC AAC CTC AAC GGG TTT       240
Ile Glu Asp Pro Pro Trp Thr Pro Cys Val Thr Asn Leu Asn Gly Phe
65              70              75              80

GTC TCC GCT TTT TTA TTC TCA ATA GAG ACA GAA ACC ACC ATT GGT TAT       288
Val Ser Ala Phe Leu Phe Ser Ile Glu Thr Glu Thr Thr Ile Gly Tyr
            85              90              95

GGC TAC AGG GTC ATC ACG GAC AAG TGC CCA GAA GGA ATC ATT CTC CTC       336
Gly Tyr Arg Val Ile Thr Asp Lys Cys Pro Glu Gly Ile Ile Leu Leu
            100             105             110

TTA ATC CAG TCC GTG TTG GGG TCC ATT GTC AAC GCC TTC ATG GTA GGA       384
Leu Ile Gln Ser Val Leu Gly Ser Ile Val Asn Ala Phe Met Val Gly
            115             120             125

TGT ATG TTT GTG AAA ATA TCC CAA CCC AAG AAG AGG GCA GAG ACC CTG       432
Cys Met Phe Val Lys Ile Ser Gln Pro Lys Lys Arg Ala Glu Thr Leu
        130             135             140

GTC TTT TCC ACC CAT GCG GTA ATC TCC ATG CGG GAT GGG AAA CTA TGC       480
Val Phe Ser Thr His Ala Val Ile Ser Met Arg Asp Gly Lys Leu Cys
145             150             155             160

CTG ATG TTC CGG GTA GGG GAC TTG AGG AAT TCC CAC ATA GTG GAG GCC       528
Leu Met Phe Arg Val Gly Asp Leu Arg Asn Ser His Ile Val Glu Ala
            165             170             175

TCC ATC AGA GCC AAG TTG ATC AAG TCC AAA CAG ACT TCA GAG GGG GAG       576
Ser Ile Arg Ala Lys Leu Ile Lys Ser Lys Gln Thr Ser Glu Gly Glu
            180             185             190

TTC ATT CCC CTC AAC CAG ACG GAT ATC AAC GTA GGG TAC TAC ACC GGG       624
Phe Ile Pro Leu Asn Gln Thr Asp Ile Asn Val Gly Tyr Tyr Thr Gly
            195             200             205

GAT GAC CGA CTC TTT CTC GTG TCA CCG CTG ATT ATT AGC CAT GAA ATT       672
Asp Asp Arg Leu Phe Leu Val Ser Pro Leu Ile Ile Ser His Glu Ile
        210             215             220

AAC CAA CAG AGT CCC TTC TGG GAG ATC TCC AAA GCC CAG CTG CCT AAA       720
Asn Gln Gln Ser Pro Phe Trp Glu Ile Ser Lys Ala Gln Leu Pro Lys
225             230             235             240

GAG GAA CTG GAG ATT GTG GTC ATC CTG GAG GGA ATG GTG GAA GCC ACA       768
Glu Glu Leu Glu Ile Val Val Ile Leu Glu Gly Met Val Glu Ala Thr
            245             250             255

GGA ATG ACG TGC CAA GCT CGA AGC TCC TAC GTC ACC AGT GAG ATC CTG       816
Gly Met Thr Cys Gln Ala Arg Ser Ser Tyr Val Thr Ser Glu Ile Leu
        260             265             270

TGG GGT TAC CGG TTC ACA CCA GTC CTG ACA CTG GAG GAC GGG TTC TAT       864
Trp Gly Tyr Arg Phe Thr Pro Val Leu Thr Leu Glu Asp Gly Phe Tyr
        275             280             285

GAA GTT GAC TAC AAC AGC TTC CAT GAG ACC CAT GAG ACC AGC ACC CCG       912
Glu Val Asp Tyr Asn Ser Phe His Glu Thr His Glu Thr Ser Thr Pro
        290             295             300

TCC CTT AGC GCC AAA GAG CTA GCC GAG CTG GCT AAC CGG GCA GAG CTG       960
Ser Leu Ser Ala Lys Glu Leu Ala Glu Leu Ala Asn Arg Ala Glu Leu
305             310             315             320

CCC CTG AGC TGG TCT GTG TCC AGC AAA CTG AAC CAA CAT GCA GAA CTG       1008
Pro Leu Ser Trp Ser Val Ser Ser Lys Leu Asn Gln His Ala Glu Leu
            325             330             335

GAG ACG GAA GAG GAA GAG AAG AAC CCG GAA GAA CTG ACA GAG AGG AAT       1056
Glu Thr Glu Glu Glu Glu Lys Asn Pro Glu Glu Leu Thr Glu Arg Asn
        340             345             350
```

```
GGT GAT GTG GCA AAC CTA GAG AAT GAG TCC AAA GTG TAG                    1095
Gly Asp Val Ala Asn Leu Glu Asn Glu Ser Lys Val
        355                 360
```

( 2 ) INFORMATION FOR SEQ ID NO:9:

( i ) SEQUENCE CHARACTERISTICS:
        ( A ) LENGTH: 364 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Asp Gly Lys Cys Asn Val His His Gly Asn Val Arg Glu Thr Tyr Arg
 1               5                  10                  15

Tyr Leu Thr Asp Ile Phe Thr Thr Leu Val Asp Leu Lys Trp Arg Phe
            20                  25                  30

Asn Leu Leu Ile Phe Val Met Val Tyr Thr Val Met Trp Leu Phe Phe
        35                  40                  45

Gly Met Ile Trp Trp Leu Ile Ala Tyr Ile Arg Gly Asp Met Asp His
 50                      55                  60

Ile Glu Asp Pro Pro Trp Thr Pro Cys Val Thr Asn Leu Asn Gly Phe
 65              70                  75                      80

Val Ser Ala Phe Leu Phe Ser Ile Glu Thr Glu Thr Thr Ile Gly Tyr
                    85                  90                  95

Gly Tyr Arg Val Ile Thr Asp Lys Cys Pro Glu Gly Ile Ile Leu Leu
            100                 105                 110

Leu Ile Gln Ser Val Leu Gly Ser Ile Val Asn Ala Phe Met Val Gly
        115                 120                 125

Cys Met Phe Val Lys Ile Ser Gln Pro Lys Lys Arg Ala Glu Thr Leu
 130                 135                 140

Val Phe Ser Thr His Ala Val Ile Ser Met Arg Asp Gly Lys Leu Cys
 145                 150                 155                 160

Leu Met Phe Arg Val Gly Asp Leu Arg Asn Ser His Ile Val Glu Ala
                165                 170                 175

Ser Ile Arg Ala Lys Leu Ile Lys Ser Lys Gln Thr Ser Glu Gly Glu
            180                 185                 190

Phe Ile Pro Leu Asn Gln Thr Asp Ile Asn Val Gly Tyr Tyr Thr Gly
        195                 200                 205

Asp Asp Arg Leu Phe Leu Val Ser Pro Leu Ile Ile Ser His Glu Ile
 210                 215                 220

Asn Gln Gln Ser Pro Phe Trp Glu Ile Ser Lys Ala Gln Leu Pro Lys
 225                 230                 235                 240

Glu Glu Leu Glu Ile Val Val Ile Leu Glu Gly Met Val Glu Ala Thr
                245                 250                 255

Gly Met Thr Cys Gln Ala Arg Ser Ser Tyr Val Thr Ser Glu Ile Leu
            260                 265                 270

Trp Gly Tyr Arg Phe Thr Pro Val Leu Thr Leu Glu Asp Gly Phe Tyr
        275                 280                 285

Glu Val Asp Tyr Asn Ser Phe His Glu Thr His Glu Thr Ser Thr Pro
 290                 295                 300

Ser Leu Ser Ala Lys Glu Leu Ala Glu Leu Ala Asn Arg Ala Glu Leu
 305                 310                 315                 320

Pro Leu Ser Trp Ser Val Ser Ser Lys Leu Asn Gln His Ala Glu Leu
                325                 330                 335
```

```
Glu Thr Glu Glu Glu Glu Lys Asn Pro Glu Glu Leu Thr Glu Arg Asn
                340                 345                 350

Gly Asp Val Ala Asn Leu Glu Asn Glu Ser Lys Val
            355                 360
```

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
Asp Ser Arg Asn Ala Met Asn Gln Asp Met Glu Ile Gly Val Thr Ser
 1               5                  10                  15

Gln Asp His Lys
            20
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
Tyr Val Arg Gly Asp Leu Asp His Val Gly Asp Gln Glu Trp Ile
 1               5                  10                  15
```

( 2 ) INFORMATION FOR SEQ ID NO:12:

( i ) SEQUENCE CHARACTERISTICS:
        ( A ) LENGTH: 1425 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 56..1330

( i x ) FEATURE:
        ( A ) NAME/KEY: misc_feature
        ( B ) LOCATION: 1..1425
        ( D ) OTHER INFORMATION: /note= "Encodes rat pancreatic beta
        cell ATP- sensitive potassium channel protein."

( x i ) SEQUENCE DESCRIPTION: SEQ ID NO:12:

```
GGTGAGGATG AAGTGAACCT ACCCTGTCCA CCACAAGGAA AAGCACAAAG AAGAA ATG    58
                                                              Met
                                                               1

ACA ATG GCC AAG TTA ACT GAA TCC ATG ACT AAT GTC CTG GAG GGG GAT    106
Thr Met Ala Lys Leu Thr Glu Ser Met Thr Asn Val Leu Glu Gly Asp
             5                  10                  15

TCC ATG GAC CAA GAC GTG GAA AGC CCA GTG GCC ATT CAC CAG CCA AAG    154
Ser Met Asp Gln Asp Val Glu Ser Pro Val Ala Ile His Gln Pro Lys
         20                  25                  30

TTG CCT AAG CAG GCC AGA GAT GAC CTG CCA AGA CAC ATC AGC CGA GAC    202
Leu Pro Lys Gln Ala Arg Asp Asp Leu Pro Arg His Ile Ser Arg Asp
     35                  40                  45

AGG ACC AAA AGG AAA ATC CAG AGG TAC GTG AGG AAG GAT GGG AAG TGT    250
Arg Thr Lys Arg Lys Ile Gln Arg Tyr Val Arg Lys Asp Gly Lys Cys
```

-continued

| | | | | | | | | | | | | | | | | |
|---|---|---|---|---|---|---|---|---|---|---|---|---|---|---|---|---|
| AAC | GTC | CAC | CAC | GGC | AAC | GTG | CGG | GAG | ACG | TAC | CGA | TAC | CTG | ACG | GAC | 298 |
| Asn | Val | His | His | Gly | Asn | Val | Arg | Glu | Thr | Tyr | Arg | Tyr | Leu | Thr | Asp | |
| | | | | 70 | | | | | 75 | | | | | 80 | | |
| ATC | TTC | ACC | ACC | CTG | GTG | GAC | CTA | AAG | TGG | AGA | TTC | AAC | CTA | TTG | ATC | 346 |
| Ile | Phe | Thr | Thr | Leu | Val | Asp | Leu | Lys | Trp | Arg | Phe | Asn | Leu | Leu | Ile | |
| | | | 85 | | | | | 90 | | | | | 95 | | | |
| TTT | GTC | ATG | GTC | TAC | ACA | GTG | ACG | TGG | CTT | TTC | TTT | GGG | ATG | ATC | TGG | 394 |
| Phe | Val | Met | Val | Tyr | Thr | Val | Thr | Trp | Leu | Phe | Phe | Gly | Met | Ile | Trp | |
| | | 100 | | | | | 105 | | | | | 110 | | | | |
| TGG | CTA | ATT | GCA | TAC | ATC | CGG | GGA | GAT | ATG | GAC | CAC | ATA | GAG | GAC | TCC | 442 |
| Trp | Leu | Ile | Ala | Tyr | Ile | Arg | Gly | Asp | Met | Asp | His | Ile | Glu | Asp | Ser | |
| | 115 | | | | | 120 | | | | | 125 | | | | | |
| CCG | TGG | ACT | CCC | TGT | GTT | ACC | AAC | CTC | AAC | GGG | TTT | GTC | TCC | GCT | TTT | 490 |
| Pro | Trp | Thr | Pro | Cys | Val | Thr | Asn | Leu | Asn | Gly | Phe | Val | Ser | Ala | Phe | |
| 130 | | | | | 135 | | | | | 140 | | | | | 145 | |
| TTA | TTC | TCA | ATA | GAG | ACA | GAA | ACC | ACC | ATT | GGT | TAT | GGC | TAC | AGG | GTC | 538 |
| Leu | Phe | Ser | Ile | Glu | Thr | Glu | Thr | Thr | Ile | Gly | Tyr | Gly | Tyr | Arg | Val | |
| | | | 150 | | | | | 155 | | | | | 160 | | | |
| ATC | ACG | GAC | AAG | TGC | CCA | GAA | GGA | ATC | ATT | CTC | CTC | TTA | ATC | CAG | TCC | 586 |
| Ile | Thr | Asp | Lys | Cys | Pro | Glu | Gly | Ile | Ile | Leu | Leu | Leu | Ile | Gln | Ser | |
| | | | 165 | | | | | 170 | | | | | 175 | | | |
| GTG | TTG | GGG | TCC | ATT | GTC | AAC | GCC | TTC | ATG | GTA | GGA | TGT | ATG | TTT | GTG | 634 |
| Val | Leu | Gly | Ser | Ile | Val | Asn | Ala | Phe | Met | Val | Gly | Cys | Met | Phe | Val | |
| | | 180 | | | | | 185 | | | | | 190 | | | | |
| AAA | ATA | TCC | CAA | CCC | AAG | AAG | AGG | GCA | GAG | ACC | CTG | GTC | TTT | TCC | ACC | 682 |
| Lys | Ile | Ser | Gln | Pro | Lys | Lys | Arg | Ala | Glu | Thr | Leu | Val | Phe | Ser | Thr | |
| | 195 | | | | | 200 | | | | | 205 | | | | | |
| CAT | GCG | GTA | ATC | TCC | ATG | CGG | GAT | GGG | AAA | CTA | TGC | CTG | ATG | TTC | CGG | 730 |
| His | Ala | Val | Ile | Ser | Met | Arg | Asp | Gly | Lys | Leu | Cys | Leu | Met | Phe | Arg | |
| 210 | | | | | 215 | | | | | 220 | | | | | 225 | |
| GTA | GGG | GAC | TTG | AGG | AAT | TCC | CAC | ATA | GTG | GAG | GCC | TCC | ATC | AGA | GCC | 778 |
| Val | Gly | Asp | Leu | Arg | Asn | Ser | His | Ile | Val | Glu | Ala | Ser | Ile | Arg | Ala | |
| | | | | 230 | | | | | 235 | | | | | 240 | | |
| AAG | TTG | ATC | AAG | TCC | AAA | CAG | ACT | TCA | GAG | GGG | GAG | TTC | ATT | CCC | CTC | 826 |
| Lys | Leu | Ile | Lys | Ser | Lys | Gln | Thr | Ser | Glu | Gly | Glu | Phe | Ile | Pro | Leu | |
| | | | 245 | | | | | 250 | | | | | 255 | | | |
| AAC | CAG | ACG | GAT | ATC | AAC | GTA | GGG | TAC | TAC | ACC | GGG | GAT | GAC | CGA | CTC | 874 |
| Asn | Gln | Thr | Asp | Ile | Asn | Val | Gly | Tyr | Tyr | Thr | Gly | Asp | Asp | Arg | Leu | |
| | | | 260 | | | | | 265 | | | | | 270 | | | |
| TTT | CTC | GTG | TCA | CCG | CTG | ATT | ATT | AGC | CAT | GAA | ATT | AAC | CAA | CAG | AGT | 922 |
| Phe | Leu | Val | Ser | Pro | Leu | Ile | Ile | Ser | His | Glu | Ile | Asn | Gln | Gln | Ser | |
| | 275 | | | | | 280 | | | | | 285 | | | | | |
| CCC | TTC | TGG | GAG | ATC | TCC | AAA | GCC | CAG | CTG | CCT | AAA | GAG | GAA | CTG | GAG | 970 |
| Pro | Phe | Trp | Glu | Ile | Ser | Lys | Ala | Gln | Leu | Pro | Lys | Glu | Glu | Leu | Glu | |
| 290 | | | | | 295 | | | | | 300 | | | | | 305 | |
| ATT | GTG | GTC | ATC | CTG | GAG | GGA | ATG | GTG | GAA | GCC | ACA | GGA | ATG | ACG | TGC | 1018 |
| Ile | Val | Val | Ile | Leu | Glu | Gly | Met | Val | Glu | Ala | Thr | Gly | Met | Thr | Cys | |
| | | | | 310 | | | | | 315 | | | | | 320 | | |
| CAA | GCT | CGA | AGC | TCC | TAC | GTC | ACC | AGT | GAG | ATC | CTG | TGG | GGT | TAC | CGG | 1066 |
| Gln | Ala | Arg | Ser | Ser | Tyr | Val | Thr | Ser | Glu | Ile | Leu | Trp | Gly | Tyr | Arg | |
| | | | 325 | | | | | 330 | | | | | 335 | | | |
| TTC | ACA | CCA | GTC | CTG | ACA | CTG | GAG | GAC | GGG | TTC | TAT | GAA | GTT | GAC | TAC | 1114 |
| Phe | Thr | Pro | Val | Leu | Thr | Leu | Glu | Asp | Gly | Phe | Tyr | Glu | Val | Asp | Tyr | |
| | | | 340 | | | | | 345 | | | | | 350 | | | |
| AAC | AGC | TTC | CAT | GAG | ACC | CAT | GAG | ACC | AGC | ACC | CCG | TCC | CTT | AGC | GCC | 1162 |
| Asn | Ser | Phe | His | Glu | Thr | His | Glu | Thr | Ser | Thr | Pro | Ser | Leu | Ser | Ala | |
| | | | 355 | | | | | 360 | | | | | 365 | | | |
| AAA | GAG | CTA | GCC | GAG | CTG | GCT | AAC | CGG | GCA | GAG | CTG | CCC | CTG | AGC | TGG | 1210 |
| Lys | Glu | Leu | Ala | Glu | Leu | Ala | Asn | Arg | Ala | Glu | Leu | Pro | Leu | Ser | Trp | |

-continued

```
                370                    375                        380                         385
        TCT GTG TCC AGC AAA CTG AAC CAA CAT GCA GAA CTG GAG ACG GAA GAG           1258
        Ser Val Ser Ser Lys Leu Asn Gln His Ala Glu Leu Glu Thr Glu Glu
                        390                     395                 400

GAA GAG AAG AAC CCG GAA GAA CTG ACA GAG AGG AAT GGT GAT GTG GCA           1306
        Glu Glu Lys Asn Pro Glu Glu Leu Thr Glu Arg Asn Gly Asp Val Ala
                        405                     410                 415

AAC CTA GAG AAT GAG TCC AAA GTG TAGACCCAGC TGGGTCAGCC TCCCCCACTC          1360
        Asn Leu Glu Asn Glu Ser Lys Val
                    420                 425

AGACATGACC CCTCCTTGTA GACCCAGCTG GGTCAACCTC TTCACTAGAT ATGACCTCCA         1420

AGCTT                                                                    1425
```

( 2 ) INFORMATION FOR SEQ ID NO:13:

( i ) SEQUENCE CHARACTERISTICS:
        ( A ) LENGTH: 425 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Thr Met Ala Lys Leu Thr Glu Ser Met Thr Asn Val Leu Glu Gly
 1               5                  10                  15

Asp Ser Met Asp Gln Asp Val Glu Ser Pro Val Ala Ile His Gln Pro
             20                  25                  30

Lys Leu Pro Lys Gln Ala Arg Asp Asp Leu Pro Arg His Ile Ser Arg
         35                  40                  45

Asp Arg Thr Lys Arg Lys Ile Gln Arg Tyr Val Arg Lys Asp Gly Lys
     50                  55                  60

Cys Asn Val His His Gly Asn Val Arg Glu Thr Tyr Arg Tyr Leu Thr
65                  70                  75                  80

Asp Ile Phe Thr Thr Leu Val Asp Leu Lys Trp Arg Phe Asn Leu Leu
                 85                  90                  95

Ile Phe Val Met Val Tyr Thr Val Thr Trp Leu Phe Phe Gly Met Ile
             100                 105                 110

Trp Trp Leu Ile Ala Tyr Ile Arg Gly Asp Met Asp His Ile Glu Asp
         115                 120                 125

Ser Pro Trp Thr Pro Cys Val Thr Asn Leu Asn Gly Phe Val Ser Ala
     130                 135                 140

Phe Leu Phe Ser Ile Glu Thr Glu Thr Thr Ile Gly Tyr Gly Tyr Arg
145                 150                 155                 160

Val Ile Thr Asp Lys Cys Pro Glu Gly Ile Ile Leu Leu Leu Ile Gln
                 165                 170                 175

Ser Val Leu Gly Ser Ile Val Asn Ala Phe Met Val Gly Cys Met Phe
             180                 185                 190

Val Lys Ile Ser Gln Pro Lys Lys Arg Ala Glu Thr Leu Val Phe Ser
         195                 200                 205

Thr His Ala Val Ile Ser Met Arg Asp Gly Lys Leu Cys Leu Met Phe
     210                 215                 220

Arg Val Gly Asp Leu Arg Asn Ser His Ile Val Glu Ala Ser Ile Arg
225                 230                 235                 240

Ala Lys Leu Ile Lys Ser Lys Gln Thr Ser Glu Gly Glu Phe Ile Pro
                 245                 250                 255

Leu Asn Gln Thr Asp Ile Asn Val Gly Tyr Tyr Thr Gly Asp Asp Arg
             260                 265                 270
```

```
Leu Phe Leu Val Ser Pro Leu Ile Ile Ser His Glu Ile Asn Gln Gln
    275                 280                 285
Ser Pro Phe Trp Glu Ile Ser Lys Ala Gln Leu Pro Lys Glu Glu Leu
    290                 295                 300
Glu Ile Val Val Ile Leu Glu Gly Met Val Glu Ala Thr Gly Met Thr
305                     310                 315                 320
Cys Gln Ala Arg Ser Ser Tyr Val Thr Ser Glu Ile Leu Trp Gly Tyr
                325                 330                     335
Arg Phe Thr Pro Val Leu Thr Leu Glu Asp Gly Phe Tyr Glu Val Asp
            340                 345                 350
Tyr Asn Ser Phe His Glu Thr His Glu Thr Ser Thr Pro Ser Leu Ser
        355                 360                 365
Ala Lys Glu Leu Ala Glu Leu Ala Asn Arg Ala Glu Leu Pro Leu Ser
    370                 375                 380
Trp Ser Val Ser Ser Lys Leu Asn Gln His Ala Glu Leu Glu Thr Glu
385                 390                 395                     400
Glu Glu Glu Lys Asn Pro Glu Glu Leu Thr Glu Arg Asn Gly Asp Val
                405                 410                 415
Ala Asn Leu Glu Asn Glu Ser Lys Val
                420             425
```

( 2 ) INFORMATION FOR SEQ ID NO:14:

( i ) SEQUENCE CHARACTERISTICS:
        ( A ) LENGTH: 1245 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 22..1242
        ( D ) OTHER INFORMATION: /note= "Encodes a full-length or
        nearly full- length human pancreatic beta cell
        ATP- sensitive potassium channel protein: Seq ID.
        15."

( x i ) SEQUENCE DESCRIPTION: SEQ ID NO:14:

```
AACGTCCTGG AGGGCGACTC C ATG GAT CAG GAC GTC GAA AGC CCA GTG GCC        51
                         Met Asp Gln Asp Val Glu Ser Pro Val Ala
                         1               5                   10

ATT CAC CAG CCA AAG TTG CCT AAG CAG GCC AGG GAT GAC CTG CCA AGA        99
Ile His Gln Pro Lys Leu Pro Lys Gln Ala Arg Asp Asp Leu Pro Arg
                15                  20                  25

CAC ATC AGC CGA GAT CGG ACC AAA AGG AAA ATC CAG AGG TAC GTG AGG       147
His Ile Ser Arg Asp Arg Thr Lys Arg Lys Ile Gln Arg Tyr Val Arg
            30                  35                  40

AAA GAC GGA AAG TGC AAT GTT CAT CAC GGC AAC GTG AGG GAG ACC TAT       195
Lys Asp Gly Lys Cys Asn Val His His Gly Asn Val Arg Glu Thr Tyr
        45                  50                  55

CGC TAC CTG ACC GAT ATC TTC ACC ACA TTA GTG GAC CTG AAG TGG AGA       243
Arg Tyr Leu Thr Asp Ile Phe Thr Thr Leu Val Asp Leu Lys Trp Arg
    60                  65                  70

TTC AAC CTA TTG ATT TTT GTC ATG GTT TAC ACA GTG ACC TGG CTC TTT       291
Phe Asn Leu Leu Ile Phe Val Met Val Tyr Thr Val Thr Trp Leu Phe
75                  80                  85                  90

TTT GGA ATG ATC TGG TGG TTG ATC GCA TAC ATA CGG GGA GAC ATG GAC       339
Phe Gly Met Ile Trp Trp Leu Ile Ala Tyr Ile Arg Gly Asp Met Asp
```

| | | | | | | | | | | | | | | | | |
|---|---|---|---|---|---|---|---|---|---|---|---|---|---|---|---|---|
| | | | | 95 | | | | | 100 | | | | | 105 | | |
| CAC | ATA | GAG | GAC | CCC | TCC | TGG | ACT | CCT | TGT | GTT | ACC | AAC | CTC | AAC | GGG | 387 |
| His | Ile | Glu | Asp 110 | Pro | Ser | Trp | Thr | Pro 115 | Cys | Val | Thr | Asn | Leu 120 | Asn | Gly | |
| TTC | GTC | TCT | GCT | TTT | TTA | TTC | TCA | ATA | GAG | ACA | GAA | ACC | ACC | ATT | GGT | 435 |
| Phe | Val | Ser 125 | Ala | Phe | Leu | Phe | Ser 130 | Ile | Glu | Thr | Glu | Thr 135 | Thr | Ile | Gly | |
| TAT | GGC | TAC | CGG | GTC | ATC | ACA | GAT | AAA | TGC | CCG | GAG | GGA | ATT | ATT | CTT | 483 |
| Tyr | Gly 140 | Tyr | Arg | Val | Ile | Thr 145 | Asp | Lys | Cys | Pro | Glu 150 | Gly | Ile | Ile | Leu | |
| CTC | TTA | ATC | CAA | TCT | GTG | TTG | GGG | TCC | ATT | GTC | AAT | GCA | TTC | ATG | GTG | 531 |
| Leu 155 | Leu | Ile | Gln | Ser | Val 160 | Leu | Gly | Ser | Ile | Val 165 | Asn | Ala | Phe | Met | Val 170 | |
| GGA | TGC | ATG | TTT | GTA | AAA | ATC | TCT | CAA | CCC | AAG | AAG | AGG | GCA | GAG | ACC | 579 |
| Gly | Cys | Met | Phe | Val 175 | Lys | Ile | Ser | Gln | Pro 180 | Lys | Lys | Arg | Ala | Glu 185 | Thr | |
| CTG | GTC | TTT | TCC | ACC | CAT | GCA | GTG | ATC | TCC | ATG | CGG | GAT | GGG | AAA | CTG | 627 |
| Leu | Val | Phe | Ser 190 | Thr | His | Ala | Val | Ile 195 | Ser | Met | Arg | Asp | Gly 200 | Lys | Leu | |
| TGC | CTG | ATG | TTC | CGG | GTA | GGG | GAC | CTT | AGG | AAT | TCC | CAC | ATT | GTG | GAG | 675 |
| Cys | Leu | Met 205 | Phe | Arg | Val | Gly | Asp 210 | Leu | Arg | Asn | Ser | His 215 | Ile | Val | Glu | |
| GCT | TCC | ATC | AGA | GCC | AAG | TTG | ATC | AAA | TCC | AAA | CAG | ACC | TCG | GAG | GGG | 723 |
| Ala | Ser | Ile | Arg 220 | Ala | Lys | Leu | Ile | Lys 225 | Ser | Lys | Gln | Thr | Ser 230 | Glu | Gly | |
| GAG | TTC | ATC | CCG | TTG | AAC | CAG | ACG | GAT | ATC | AAC | GTA | GGG | TAT | TAC | ACG | 771 |
| Glu 235 | Phe | Ile | Pro | Leu | Asn 240 | Gln | Thr | Asp | Ile | Asn 245 | Val | Gly | Tyr | Tyr | Thr 250 | |
| GGG | GAT | GAC | CGT | CTG | TTT | CTG | GTG | TCA | CCG | CTG | ATC | ATT | AGC | CAT | GAA | 819 |
| Gly | Asp | Asp | Arg | Leu 255 | Phe | Leu | Val | Ser | Pro 260 | Leu | Ile | Ile | Ser | His 265 | Glu | |
| ATT | AAC | CAA | CAG | AGT | CCT | TTC | TGG | GAG | ATC | TCC | AAA | GCC | CAG | CTG | CCC | 867 |
| Ile | Asn | Gln | Gln | Ser 270 | Pro | Phe | Trp | Glu | Ile 275 | Ser | Lys | Ala | Gln | Leu 280 | Pro | |
| AAA | GAG | GAA | CTG | GAA | ATT | GTG | GTC | ATC | CTA | GAA | GGA | ATG | GTG | GAA | GCC | 915 |
| Lys | Glu | Glu 285 | Leu | Glu | Ile | Val | Val 290 | Ile | Leu | Glu | Gly | Met 295 | Val | Glu | Ala | |
| ACA | GGG | ATG | ACA | TGC | CAA | GCT | CGA | AGC | TCC | TAC | ATC | ACC | AGT | GAG | ATC | 963 |
| Thr | Gly | Met 300 | Thr | Cys | Gln | Ala 305 | Arg | Ser | Ser | Tyr | Ile 310 | Thr | Ser | Glu | Ile | |
| CTG | TGG | GGT | TAC | CGG | TTC | ACA | CCT | GTC | CTG | ACC | CTG | GAG | GAC | GGG | TTC | 1011 |
| Leu 315 | Trp | Gly | Tyr | Arg | Phe 320 | Thr | Pro | Val | Leu | Thr 325 | Leu | Glu | Asp | Gly | Phe 330 | |
| TAC | GAA | GTT | GAC | TAC | AAC | AGC | TTC | CAT | GAG | ACC | TAT | GAG | ACC | AGC | ACC | 1059 |
| Tyr | Glu | Val | Asp | Tyr 335 | Asn | Ser | Phe | His | Glu 340 | Thr | Tyr | Glu | Thr | Ser 345 | Thr | |
| CCA | TCC | CTT | AGT | GCC | AAA | GAG | CTG | GCC | GAG | TTA | GCC | AGC | AGG | GCA | GAG | 1107 |
| Pro | Ser | Leu | Ser 350 | Ala | Lys | Glu | Leu | Ala 355 | Glu | Leu | Ala | Ser | Arg 360 | Ala | Glu | |
| CTG | CCC | CTG | AGT | TGG | TCT | GTA | TCC | AGC | AAA | CTC | AAC | CAA | CAT | GCA | GAA | 1155 |
| Leu | Pro | Leu 365 | Ser | Trp | Ser | Val | Ser 370 | Ser | Lys | Leu | Asn | Gln 375 | His | Ala | Glu | |
| CTG | GAG | ACT | GAA | GAG | GAA | GAA | AAG | AAC | CTC | GAA | GAG | CAA | ACA | GAA | AGA | 1203 |
| Leu | Glu 380 | Thr | Glu | Glu | Glu 385 | Glu | Lys | Asn | Leu | Glu 390 | Glu | Gln | Thr | Glu | Arg | |
| AAT | GGT | GAT | GTG | GCA | AAC | CTG | GAG | AAT | GAA | TCC | AAA | GTT | TAG | | | 1245 |
| Asn 395 | Gly | Asp | Val | Ala 400 | Asn | Leu | Glu | Asn | Glu 405 | Ser | Lys | Val | | | | |

( 2 ) INFORMATION FOR SEQ ID NO:15:

( i ) SEQUENCE CHARACTERISTICS:
  ( A ) LENGTH: 407 amino acids
  ( B ) TYPE: amino acid
  ( D ) TOPOLOGY: linear ( i i ) MOLECULE TYPE: protein ( x i ) SEQUENCE DESCRIPTION: SEQ ID NO:15:

| Met | Asp | Gln | Asp | Val | Glu | Ser | Pro | Val | Ala | Ile | His | Gln | Pro | Lys | Leu |
| 1 | | | | 5 | | | | | 10 | | | | | 15 | |

| Pro | Lys | Gln | Ala | Arg | Asp | Asp | Leu | Pro | Arg | His | Ile | Ser | Arg | Asp | Arg |
| | | | 20 | | | | | 25 | | | | | 30 | | |

| Thr | Lys | Arg | Lys | Ile | Gln | Arg | Tyr | Val | Arg | Lys | Asp | Gly | Lys | Cys | Asn |
| | | | 35 | | | | 40 | | | | | 45 | | | |

| Val | His | His | Gly | Asn | Val | Arg | Glu | Thr | Tyr | Arg | Tyr | Leu | Thr | Asp | Ile |
| | | 50 | | | | | 55 | | | | | 60 | | | |

| Phe | Thr | Thr | Leu | Val | Asp | Leu | Lys | Trp | Arg | Phe | Asn | Leu | Leu | Ile | Phe |
| 65 | | | | | 70 | | | | | 75 | | | | | 80 |

| Val | Met | Val | Tyr | Thr | Val | Thr | Trp | Leu | Phe | Phe | Gly | Met | Ile | Trp | Trp |
| | | | | 85 | | | | | 90 | | | | | 95 | |

| Leu | Ile | Ala | Tyr | Ile | Arg | Gly | Asp | Met | Asp | His | Ile | Glu | Asp | Pro | Ser |
| | | | | 100 | | | | | 105 | | | | | 110 | |

| Trp | Thr | Pro | Cys | Val | Thr | Asn | Leu | Asn | Gly | Phe | Val | Ser | Ala | Phe | Leu |
| | | | 115 | | | | | 120 | | | | | 125 | | |

| Phe | Ser | Ile | Glu | Thr | Glu | Thr | Thr | Ile | Gly | Tyr | Gly | Tyr | Arg | Val | Ile |
| | | 130 | | | | | 135 | | | | | 140 | | | |

| Thr | Asp | Lys | Cys | Pro | Glu | Gly | Ile | Ile | Leu | Leu | Leu | Ile | Gln | Ser | Val |
| 145 | | | | | 150 | | | | | 155 | | | | | 160 |

| Leu | Gly | Ser | Ile | Val | Asn | Ala | Phe | Met | Val | Gly | Cys | Met | Phe | Val | Lys |
| | | | | 165 | | | | | 170 | | | | | 175 | |

| Ile | Ser | Gln | Pro | Lys | Lys | Arg | Ala | Glu | Thr | Leu | Val | Phe | Ser | Thr | His |
| | | | 180 | | | | | 185 | | | | | 190 | | |

| Ala | Val | Ile | Ser | Met | Arg | Asp | Gly | Lys | Leu | Cys | Leu | Met | Phe | Arg | Val |
| | | | 195 | | | | | 200 | | | | | 205 | | |

| Gly | Asp | Leu | Arg | Asn | Ser | His | Ile | Val | Glu | Ala | Ser | Ile | Arg | Ala | Lys |
| | 210 | | | | | 215 | | | | | 220 | | | | |

| Leu | Ile | Lys | Ser | Lys | Gln | Thr | Ser | Glu | Gly | Glu | Phe | Ile | Pro | Leu | Asn |
| 225 | | | | | 230 | | | | | 235 | | | | | 240 |

| Gln | Thr | Asp | Ile | Asn | Val | Gly | Tyr | Tyr | Thr | Gly | Asp | Asp | Arg | Leu | Phe |
| | | | | 245 | | | | | 250 | | | | | 255 | |

| Leu | Val | Ser | Pro | Leu | Ile | Ile | Ser | His | Glu | Ile | Asn | Gln | Gln | Ser | Pro |
| | | | 260 | | | | | 265 | | | | | 270 | | |

| Phe | Trp | Glu | Ile | Ser | Lys | Ala | Gln | Leu | Pro | Lys | Glu | Glu | Leu | Glu | Ile |
| | | 275 | | | | | 280 | | | | | 285 | | | |

| Val | Val | Ile | Leu | Glu | Gly | Met | Val | Glu | Ala | Thr | Gly | Met | Thr | Cys | Gln |
| | 290 | | | | | 295 | | | | | 300 | | | | |

| Ala | Arg | Ser | Ser | Tyr | Ile | Thr | Ser | Glu | Ile | Leu | Trp | Gly | Tyr | Arg | Phe |
| 305 | | | | | 310 | | | | | 315 | | | | | 320 |

| Thr | Pro | Val | Leu | Thr | Leu | Glu | Asp | Gly | Phe | Tyr | Glu | Val | Asp | Tyr | Asn |
| | | | | 325 | | | | | 330 | | | | | 335 | |

| Ser | Phe | His | Glu | Thr | Tyr | Glu | Thr | Ser | Thr | Pro | Ser | Leu | Ser | Ala | Lys |
| | | | 340 | | | | | 345 | | | | | 350 | | |

| Glu | Leu | Ala | Glu | Leu | Ala | Ser | Arg | Ala | Glu | Leu | Pro | Leu | Ser | Trp | Ser |
| | | 355 | | | | | 360 | | | | | 365 | | | |

| Val | Ser | Ser | Lys | Leu | Asn | Gln | His | Ala | Glu | Leu | Glu | Thr | Glu | Glu | Glu |

| | | | | | | | | | | | | | |
|---|---|---|---|---|---|---|---|---|---|---|---|---|---|
| | | 370 | | | | 375 | | | | | 380 | | |
| Glu | Lys | Asn | Leu | Glu | Glu | Gln | Thr | Glu | Arg | Asn | Gly | Asp | Val | Ala | Asn |
| 385 | | | | | 390 | | | | 395 | | | | 400 |
| Leu | Glu | Asn | Glu | Ser | Lys | Val |
| | | | | 405 | | |